United States Patent [19]
Yabe et al.

[11] Patent Number: 5,458,132
[45] Date of Patent: Oct. 17, 1995

[54] ENDOSCOPE COVER-SHEATHED ENDOSCOPE SYSTEM

[75] Inventors: Hisao Yabe, Hachioji; Yoshihiro Iida, Tama; Akira Suzuki; Hideo Itoh, both of Hachioji; Yoshio Tashiro, Hino; Minoru Yamazaki; Osamu Tamada, both of Hachioji, all of Japan

[73] Assignee: Olympus Optical Co., Ltd., Tokyo, Japan

[21] Appl. No.: 52,710

[22] Filed: Apr. 27, 1993

[30] Foreign Application Priority Data

Mar. 15, 1993 [JP] Japan .................. 5-011193 U
Mar. 15, 1993 [JP] Japan .................. 5-054354

[51] Int. Cl.⁶ .................................................. A61B 1/00
[52] U.S. Cl. .................................................. 600/121
[58] Field of Search ................................. 128/4, 6, 844, 128/917, 918, 919; 604/263

[56] References Cited

U.S. PATENT DOCUMENTS

| | | |
|---|---|---|
| Re. 34,110 | 9/1992 | Opie . |
| 3,162,190 | 12/1964 | Del Gizzo . |
| 4,646,722 | 3/1987 | Silverstein et al. ............ 128/4 |
| 4,721,097 | 1/1988 | D'Amelio ..................... 128/4 |
| 4,741,326 | 5/1988 | Sidall et al. .................. 128/4 |
| 4,825,850 | 5/1989 | Opie et al. .................... 128/4 |
| 4,869,238 | 9/1989 | Opie ........................... 128/6 |
| 4,877,033 | 10/1989 | Seitz, Jr. .................... 128/4 X |
| 4,878,485 | 11/1989 | Adair ......................... 128/6 |
| 4,886,049 | 12/1989 | Darras ........................ 128/4 |
| 4,907,395 | 3/1990 | Opie ........................ 53/434 |
| 4,991,564 | 2/1991 | Takahashi ..................... 128/4 |
| 4,991,565 | 2/1991 | Takahashi ..................... 128/4 |
| 4,997,084 | 3/1991 | Opie ......................... 206/364 |
| 5,050,585 | 9/1991 | Takahashi ..................... 128/4 |
| 5,058,567 | 10/1991 | Takahashi ..................... 128/4 |
| 5,168,803 | 12/1992 | Kurtzer ....................... 128/4 |
| 5,198,894 | 3/1993 | Hicks ....................... 128/4 X |
| 5,237,984 | 8/1993 | Williams, III et al. ........... 128/4 |
| 5,359,991 | 11/1994 | Takahashi et al. ............... 128/4 |

FOREIGN PATENT DOCUMENTS

| | | |
|---|---|---|
| 0184778 | 6/1986 | European Pat. Off. . |
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |

(List continued on next page.)

Primary Examiner—Richard J. Apley
Assistant Examiner—Beverly M. Flanagan
Attorney, Agent, or Firm—Armstrong, Westerman, Hattori, McLeland & Naughton

[57] ABSTRACT

The present invention relates to an endoscope cover-sheathed endoscope having an endoscope in which an insertional part is extending from an operational part, and an endoscope cover made up of an insertional part cover, an operational part cover, and a universal cord cover, which shield the endoscope and are concatenated in that order from the distal end of the endoscope.

The operational part cover overlaps and shields the margin of the insertional part cover, while the operational part cover overlaps and shields the margin of the universal cord cover. The endoscope will not therefore be bared.

The proximal portion of an insertional part cover skin of the insertional part cover, which shields the insertional part and consists of a distal part, an insertional part cover skin, and an operational endoscope cover locking cap, is formed as a rigid skin made of Teflon, urethane, or other resin having such rigidity that will not cause a damage resulting from friction with other member, for example, a rigid sheath.

6 Claims, 20 Drawing Sheets

U.S. PATENT DOCUMENTS

| | | |
|---|---|---|
| 62-177701 | 11/1987 | Japan . |
| 1-140902 | 9/1989 | Japan . |
| 2-57228 | 2/1990 | Japan . |
| 2-54734 | 11/1990 | Japan . |
| 3-13105 | 2/1991 | Japan . |
| 3-37030 | 2/1991 | Japan . |
| 3-37029 | 2/1991 | Japan . |
| 3-29635 | 2/1991 | Japan . |
| 3-29634 | 2/1991 | Japan . |
| 3-221024 | 9/1991 | Japan . |
| 3-101906 | 10/1991 | Japan . |
| 3-101907 | 10/1991 | Japan . |
| 3-101905 | 10/1991 | Japan . |
| 3-101904 | 10/1991 | Japan . |
| 3-101903 | 10/1991 | Japan . |
| 3-101902 | 10/1991 | Japan . |
| 3-101901 | 10/1991 | Japan . |
| H4-325138 | 11/1992 | Japan . |

ENDOSCOPE COVER-SHEATHED ENDOSCOPE SYSTEM

BACKGROUND OF THE INVENTION

1. Field of the Invention

The present invention relates to an endoscope cover-sheathed endoscope system having an endoscope cover for use in sheathing an endoscope.

2. Description of the Related Art

In recent years, endoscopes have been widely adopted in the field of medicine. When an endoscope designed for medical use is employed to conduct an endoscopic examination, the endoscope must be thoroughly cleaned and disinfected before examination.

An air/water supply channel and a forceps channel are usually formed in an endoscope, which poses a drawback that it takes much time to thoroughly clean or sterilize these channels and their insides alike after use. Unless sterilization is performed thoroughly, satisfactory effects are not expected. The sterilization cannot help therefore being continued for a prolonged period of time. This deteriorates the use efficiency of an endoscope. Besides, the work of sterilization is a nuisance.

In consideration of the foregoing drawbacks, an endoscope cover-sheathed endoscope system has been proposed in, for example, Japanese Patent Publication No. 1990-54734 and U.S. Pat. Nos. 3,162.190, 5,050,585 and 4,646,722, wherein an endoscope is used with its body sheathed with an endoscope cover, the endoscope cover alone is disposed of after every use so that the endoscope body will not become dirty, and thus either cleaning or sterilization need not be done.

To be more specific, the insertional part of an endoscope-cover coverable endoscope to be sheathed with an endoscope cover is cleaned or sterilized beforehand, sheathed with the endoscope cover, and then inserted into a patient's body cavity to carry out examination or treatment. Thus, the endoscope will not touch the patient's body cavity directly. After use, the endoscope cover used to shield the endoscope body is removed and disposed of. Thus, since an endoscope cover is disposable for each patient, an endoscope need not be cleaned or disinfected but handled very conveniently.

The aforesaid endoscope cover usually consists of multiple cover members; such as, an insertional part cover, a operational part cover, and an universal cord cover linked with one another in that order from the distal end of the endoscope cover. In this arrangement, a conventional endoscope cover-sheathed endoscope system has not been designed to take care of a junction between each pair of adjoining cover members. An endoscope is therefore exposed to the outside at a border between adjoining cover members.

In the above case, since the endoscope is not sterilized before use, bacteria may adhere to the endoscope. If gloves or bare fingers touch the bared portion, bacteria adhere to the gloves or bare fingers. The bacteria may eventually adhere to the surface of an endoscope cover via the gloves or bare fingers.

To avoid the above incident, a user must handle an endoscope with extreme care so as not to touch an bared portion of the endoscope. Alternatively, a sterilized endoscope must be used with it sheathed with an endoscope cover.

In the aforesaid endoscope cover, a conventional cover skin for shielding the insertional part of an endoscope is realized with a thin membranous member made of a soft material. For example, Japanese Patent Publication No. 1990-54734 has proposed an endoscope cover consisting of a rigid cover fitted into a distal structure of an endoscope so as to shield the distal structure and a flexible cylindrical shielding member for shielding an insertional part formed at the proximal end of the rigid cover.

The foregoing endoscope cover-sheathed endoscope has been utilized for various applications. For observation of an abdominal cavity, for example, a distally-bending rigid scope sheathed with an endoscope cover is inserted into the abdominal cavity via a trocar or other rigid sheath punctured at the patient's abdomen. In this observation, generally, air is supplied to inflate the abdominal cavity for clear visualization, and then a field of view is focused. The air supplied to the abdominal cavity must not leak out of a gap between the rigid sheath and endoscope cover. An airtight packing is mounted in the rigid sheath to block the gap between the rigid sheath and endoscope cover, thus ensuring airtightness.

A soft endoscope covert has been used to sheath a conventional laparoscope. When the laparoscope is inserted into a rigid sheath or operated with it inserted into a rigid sheath, if an attempt is made to insert, remove, or manipulate the laparoscope forcibly, the endoscope cover wrinkles because a frictional force is exerted in an area in which the cover skin of the endoscope cover rubs against the airtight packing. If the laparoscope is handled further Forcibly, the endoscope cover may be pierced or damaged. To avoid these incidents, a laparoscope must be inserted into or removed from a rigid sheath, or manipulated very carefully.

SUMMARY OF THE INVENTION

A first object of the invention is to provide a user-friendly endoscope cover-sheathed endoscope system in which an endoscope will not be exposed to the outside at a junction between cover members but can be used without any special care.

A second object of the present invention is to provide an endoscope cover-sheathed endoscope system in which an insertional part shield will not be damaged with a frictional force when coming into contact with the other member.

A third object of the present invention is to provide an endoscope cover-sheathed endoscope system in which cover members will not be deviated from each other at a junction between them.

A Fourth object of the present invention is to provide an endoscope cover-sheathed endoscope system in which cover members fixed overlapping each other can be removed without tears.

A fifth object of the present invention is to provide an endoscope cover-sheathed endoscope system in which when an endoscope is inserted via a rigid sheath, an insertional part shield will not be damaged with a frictional force.

A sixth object of the present invention is to provide an endoscope cover-sheathed endoscope having an endoscope whose insertional part shield will not be damaged when coming into contact with other member and whose distal part can be bent.

Briefly, the present invention is an endoscope cover-sheathed endoscope system having an endoscope in which an insertional part is extending from an operational part, and an endoscope cover for shielding the endoscope. At a junction between at least a pair of cover members among multiple cover members constituting the endoscope cover, a second cover member overlaps and shields the margin of a first cover member. Alternatively, a rigid shield made of a material having rigidity that will not cause a damage resulting from friction with other member is provided for at least part of an insertional part shield of the endoscope cover for shielding an insertional part of an endoscope.

The other objects and advantages of the present invention will become further apparent from the detailed explanation below.

BRIEF DESCRIPTION OF THE DRAWINGS

FIG. 1 is an oblique view for explaining an overall configuration of an endoscope cover-sheathed endoscope system;

FIG. 2 is a perspective view showing a state in which an endoscope cover and an angling knob are put in a packing case:

FIG. 3 is a longitudinal cross-sectional view showing an insertional part cover of an endoscope cover with which an endoscope-cover coverable endoscope is sheathed;

FIG. 4 is an enlarged side view showing a junction between an insertional part cover and an operational cover and a junction between a universal cord cover and an operational part cover;

FIG. 5 is a side view showing a coverable endoscope with an angling knob mounted;

FIG. 8 is a longitudinal cross-sectional view showing an operational part cover and attachment jigs for use in attaching the operational part cover to an operational part;

FIG. 9 is a longitudinal cross-sectional view of an attachment jig;

FIG. 10 is a side view showing a state in which attachment jigs are used to start attaching an operational part cover to an operational part;

FIG. 11 is a side view showing a state in which an operational part cover is being attached to an operational part using attachment jigs;

FIG. 12 is a side view showing a state in which an operational part cover has been attached to an operational part using attachment jigs;

FIG. 16 is a longitudinal cross-sectional view for explaining an overall configuration of an endoscope cover-sheathed endoscope system using an endoscope-cover coverable distally-bending rigid scope;

FIG. 17 is a longitudinal cross-sectional view showing an insertional part cover of an endoscope cover attached to an endoscope-cover coverable distally-bending rigid scope;

FIG. 18 is a longitudinal cross-sectional view showing a scene in which an endoscope-cover coverable distally-bending rigid scope, which is sheathed with a cover, is inserted into a patient's abdominal cavity via a rigid sheath;

FIG. 19 is an enlarged side view of an endoscope-cover coverable distally-bending rigid scope showing a junction between an insertional part cover and an operational part cover and a junction between a universal cord cover and an operational part cover;

FIG. 20 is a side view showing an endoscope-cover coverable distally-bending rigid scope;

FIG. 22 is a side view showing other embodiment of an endoscope-cover coverable distally-bending rigid scope;

FIG. 23 is a longitudinal cross-sectional view showing a state in which an endoscope-cover coverable distally-bending rigid scope is sheathed with an endoscope cover;

FIG. 24 shows an a cross section of FIG. 23;

FIG. 25 is a longitudinal cross-sectional view showing an angling mechanism schematically; and FIG. 26 is a longitudinal cross-sectional view showing the vicinity of a distal part of an endoscope-cover coverable distally-bending rigid scope.

DETAILED DESCRIPTION OF THE PREFERRED EMBODIMENTS

Embodiments of the present invention will be described with reference to the drawings.

Figure 1:
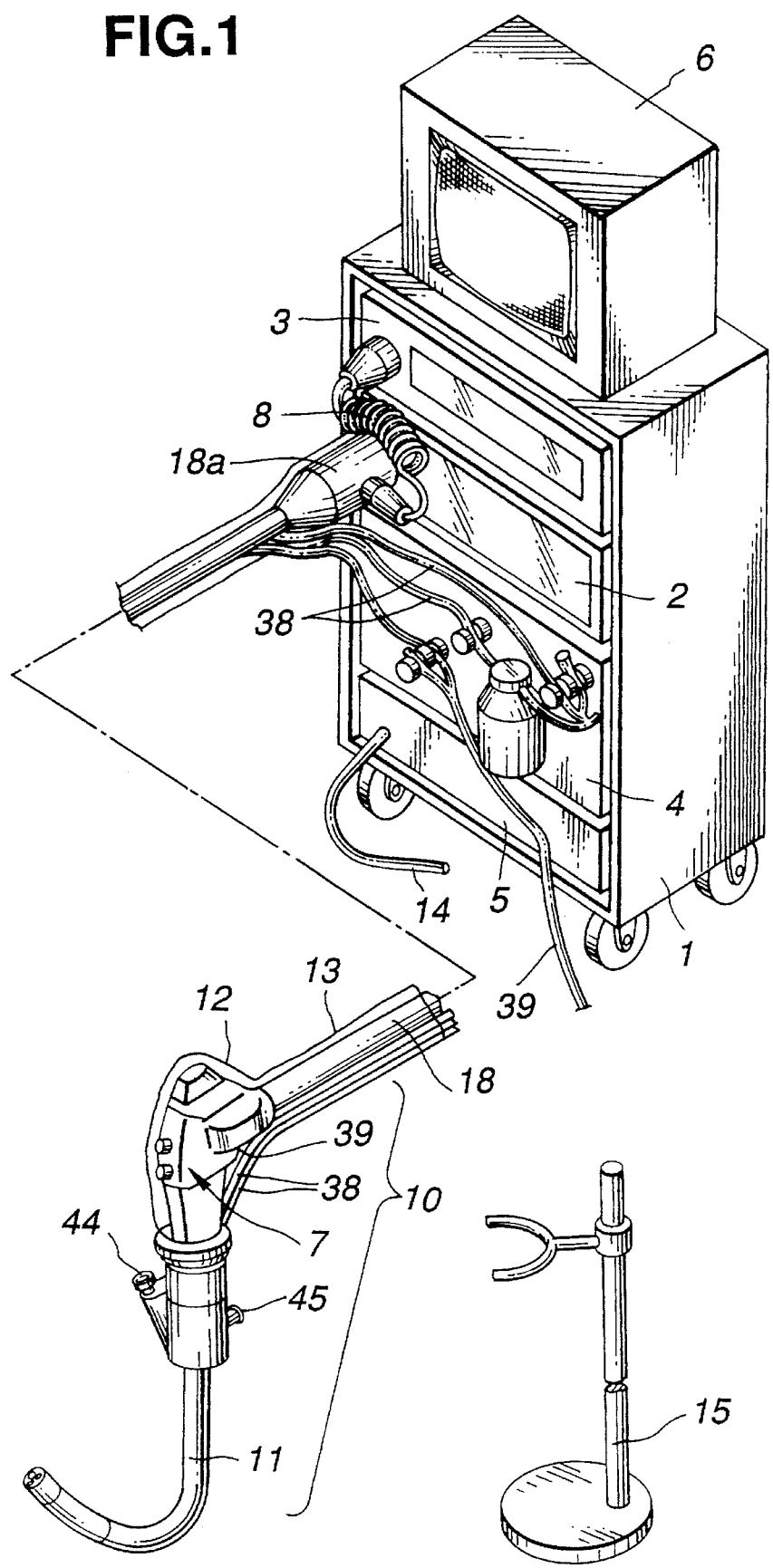
FIGS. 1 to 5 relate to the first embodiment of the present invention.
Figure 2:
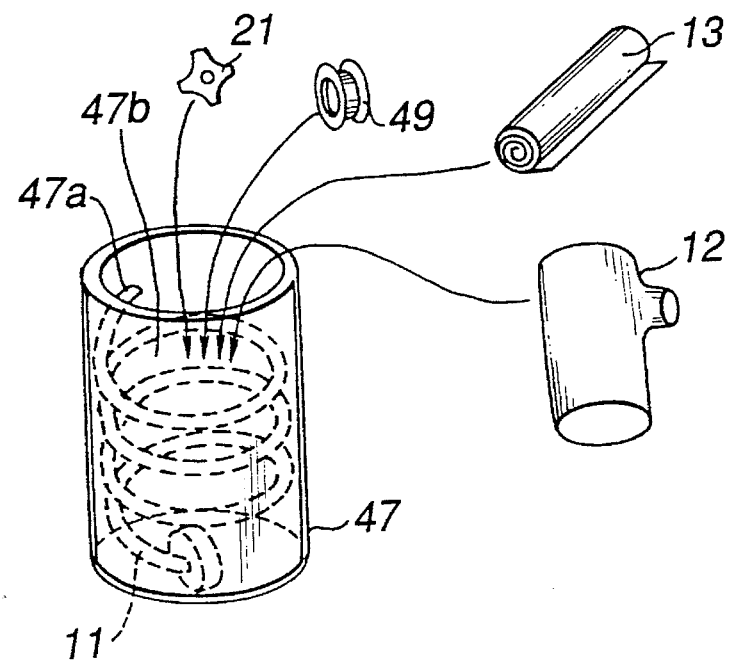
Figure 3:
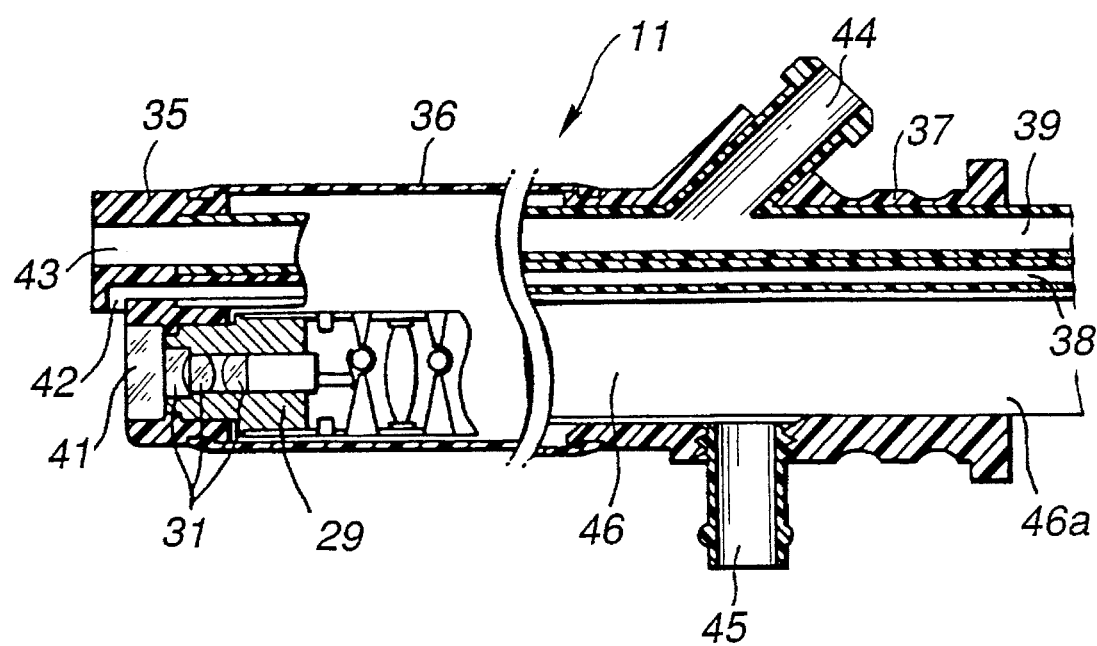
Figure 4:
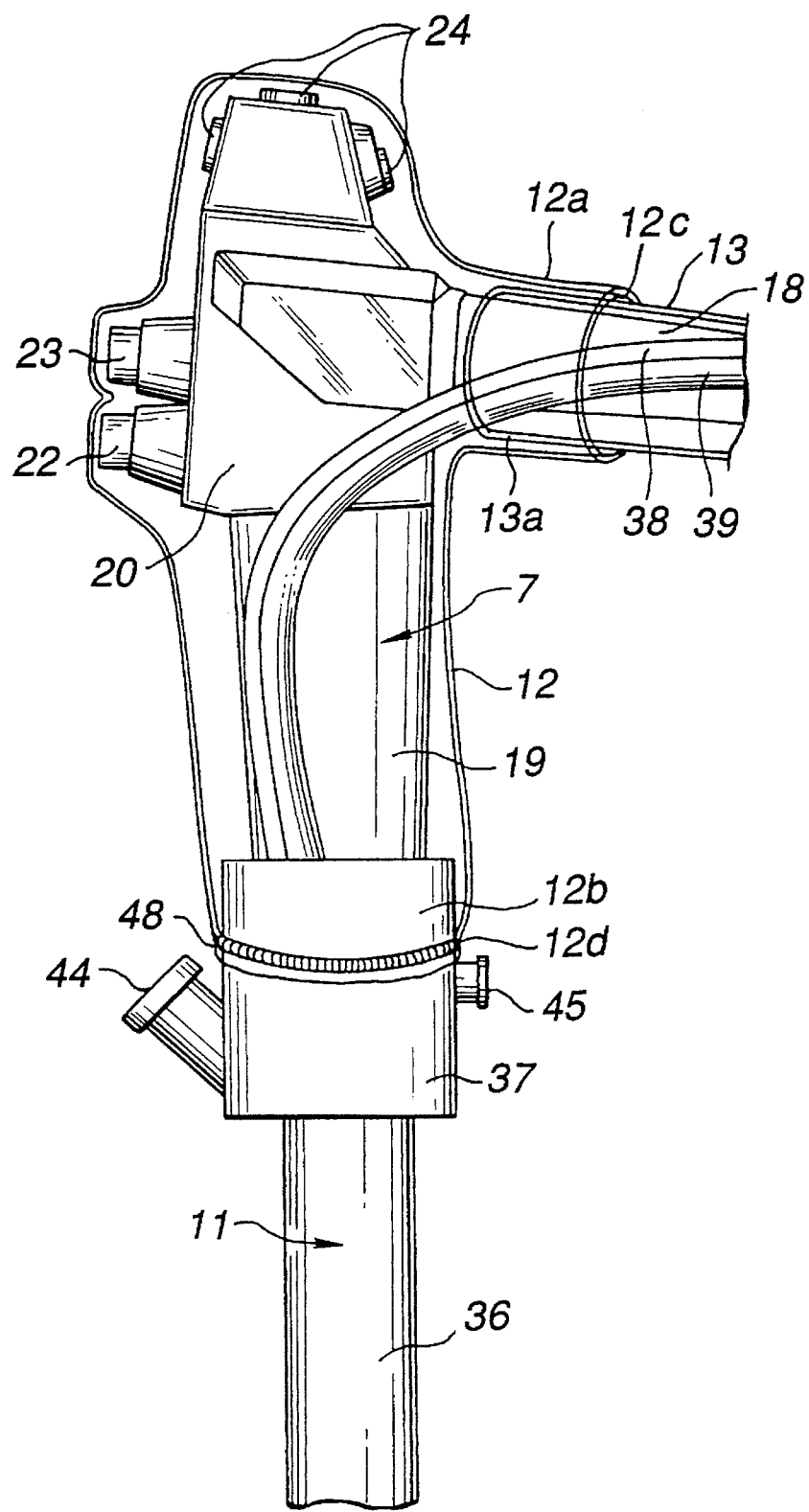
Figure 5:
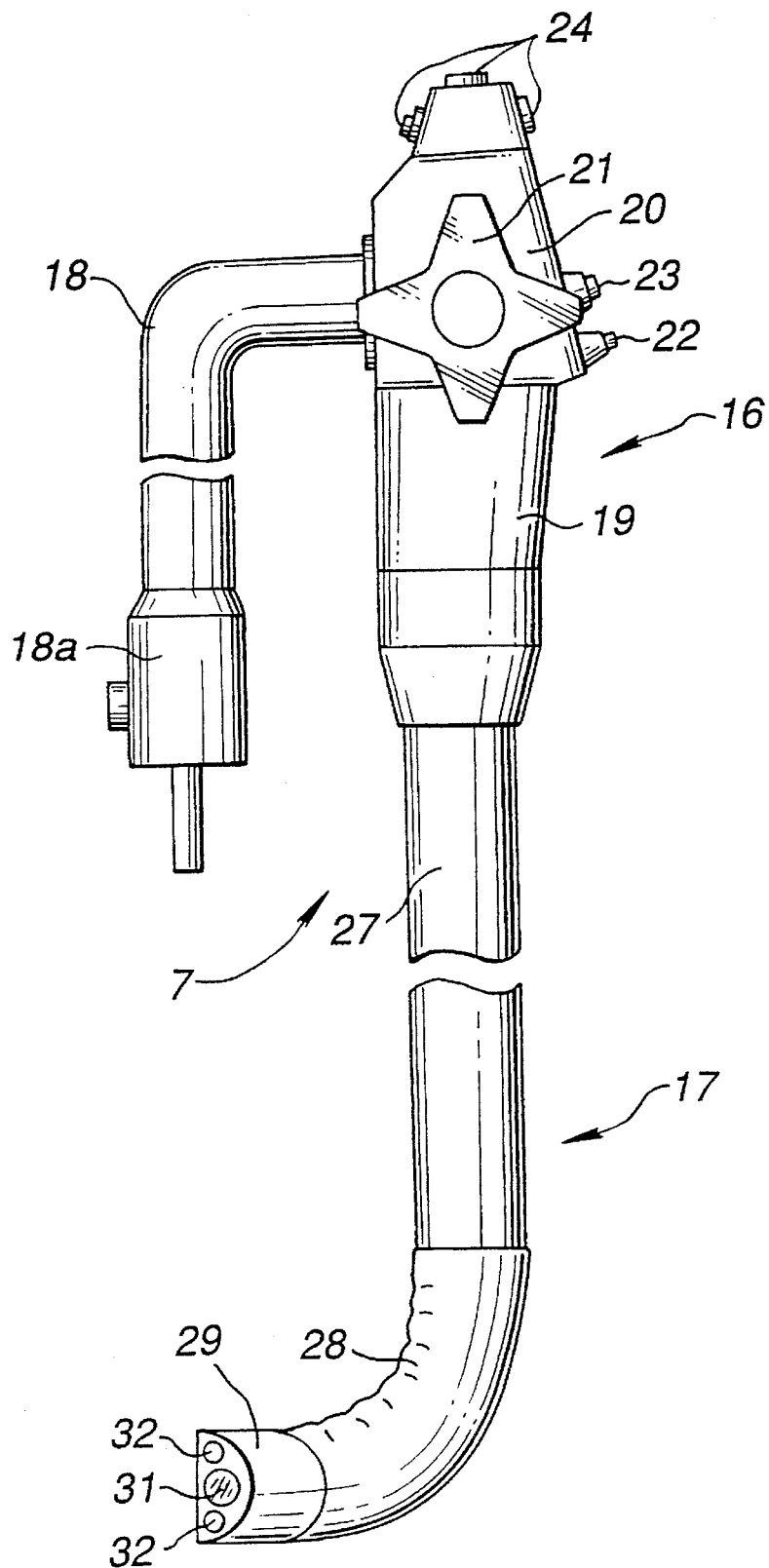

FIGS. 1 to 5 relate to the first embodiment of the present invention. FIG. 1 is an oblique view for explaining an overall configuration of an endoscope cover-sheathed endoscope system. FIG. 2 is an oblique view showing a state in which an endoscope cover and an angling knob are put in a packing case. FIG. 3 is a longitudinal cross-sectional view showing an insertional part cover of an endoscope cover (hereinafter, cover) attached to an endoscope-cover coverable endoscope. FIG. 4 is an enlarged side view showing a junction between an insertional part cover and an operational part cover and a Junction between a universal cord cover and an operational cover. FIG. 5 is a side view showing a coverable endoscope with an angling knob mounted.

An endoscope system according to the first embodiment consists mainly of, for example, a light source apparatus 2 with a built-in light source for illuminating a subject, a video processor 3 for processing signals sent from an imaging device which is not shown, and a fluid control apparatus 4 for controlling air/water supply, an endoscope cover dilator (hereinafter, dilator) from which an extension tube 14 is extending, and a monitor 6 for observing images, which are stored in or placed on a movable cart 1. An endoscope-cover coverable endoscope (hereinafter, coverable endoscope) is connected to the light source apparatus 2.

The coverable endoscope 7 has an elongated insertional part 17 extending from an operational part 16 formed at the proximal end thereof, and a universal cord 18 extending from the side of the operational part 16.

The insertional part 17 consists of a flexible portion 27, a bending portion 28, and a distal structure 29, which are concatenated in that order from the proximal end toward the distal end thereof. The bending portion 28 is angled by manipulating an angling knob 21. The distal structure 29 includes an objective optical system 31 and multiple illumination optical systems 32.

On the other hand, a connector 18a is formed at the distal end of the universal cord 18 and plugged into the light source apparatus 2. The connector 18a is also connected to the video processor 3 via a cable 8 extending from the side thereof, whereby the output signal of an imaging device, which is not shown, incorporated in the distal structure 29 of the insertional part 17 is transmitted and supplied to the video processor 3.

In the operational part 16, a grip 19 for gripping the endoscope 7 is linked with the distal end of an operational part body 20. The operational part body 20 has an angling knob 21, an air/water control switch 22, a suction control switch 23, and an image selection switch 24 for selecting a still image or the like. The angling knob 21 can be dismounted freely from the operational part body 20.

An endoscope cover 10 attached to the aforesaid endoscope 7, as shown in FIG. 1, consists mainly of an insertional part cover 11, an operational part cover 12, and a universal cord cover 13, which are concatenated in that order from the distal end thereof. The detail of the insertional part cover 11 of the cover 10 will be described with reference to FIG. 3. The coverable endoscope 7 is sheathed with the insertional cover 11 held by a cover holding instrument 15 (See FIG. 1). An endoscope cover-sheathed endoscope (hereinafter, covered endoscope) is formed by sheathing the coverable endoscope 7 with the cover 10.

As shown in FIG. 3, the insertional part cover 11 has a distal part 35 made of a relatively rigid resin, an insertional part cover skin 36 made of a soft thin membranous high polymer material, and an operational endoscope part locking cap 37 made of a rigid resin, which are concatenated in that order from the distal end thereof. The margins of the insertional part cover skin 36 are coupled with the distal part 35 and insertional endoscope part locking cap 37 so as to tightly shut out water and air. An endoscope insertion channel 46 for inserting the endoscope 7 is formed in the distal part 45, insertional part cover skin 36 and operational endoscope part locking cap 37. An air/water supply channel 38 made of a soft resin and a suction channel 39 made also of a soft resin are also running through the insertional part cover 11.

The distal part 35 has an observation window 41, which is made of a transparent resin, facing forward along the optical axes of the objective optical system 31 and illumination optical systems 32 of the coverable endoscope. An air/water nozzle (hereinafter, nozzle) 42 opens onto the window 41 to clean the observation window 41. A forceps outlet 43 is formed to communicate with the suction channel 39.

The operational endoscope part locking cap 37 has a forceps insertion port 44 made of a rigid resin, and an extension tube cap 45 with which an extension tube 14 of a dilator 5 is coupled and that is made of a rigid resin. An opening 46a of the endoscope insertion channel 46 is formed at the proximal end of the cap 37. The air/water supply channel 38 and suction channel 39 are extending beyond the proximal end of the cap 37.

FIG. 4 is an enlarged side view showing the junctions between the insertional part cover 11 and operational part cover 12, and between the universal cord cover 13 and operational part cover 12. As illustrated, the operational part cover 1.2 is a sack-like member made of a soft high polymer material. A universal cord-side margin 12a has a universal cord opening 12c that is an opening for inserting the universal cord 18, and an insertional part-side margin 12b has an endoscope opening 12d for inserting the coverable endoscope 7. The operational part cover 12 has a hole through which the angling knob 44 is mounted on the coverable endoscope 7.

The universal cord-side margin 12a of the operational cover 12 is extending to shield part of the universal cord 18 with the universal cord cover 13 between them. A margin 13a of the universal cord cover 13 underlies the operational cover 12 and is completely shielded thereby. On the other hand, the insertional part-side margin 12b of the operational cover 12 shields the operational part-side margin of the operational endoscope part locking cap 37 and extends to the vicinity of the dilation tube cap 45. An elastic ring 48 that is stretchable radially blocks the endoscope opening 12d.

The universal cord cover 13 is a cylindrical member that is made of a soft thin membranous high polymer material and whose ends are open. The universal cord cover 13 is as long as or is slightly longer than the universal cord 18. The inner diameter and the diameters of the openings of the universal cord cover 13 are slightly larger than the outer diameter of the connector 18a.

A coverable endoscope to which this embodiment applies is not limited to the coverable endoscope 7 sheathed with the cover 10. The embodiment is also applicable to an uncovered endoscope, which is usually used without a cover, may be sheathed with a cover.

FIG. 2 shows an example of a packing material for a cover 10 and an example of putting components in the packing material.

As illustrated, a packing case 47 is a bottomed cylinder made of a high polymer material, paper, or other material having air permeability. The packing case 47 has multiple holes each having a diameter of 0.2 micrometer to ensure air permeability but not to pass bacteria. A spiral storage 47a is formed on the inner surface of the packing case 47, wherein the insertional, part cover 11 is wound spirally and stored in constant pitches.

A space created inside the insertional part cover 11 wound spirally; that is, a space inside the spiral storage 47a serves as an accessory storage 47b for storing the operational part cover 12, universal cord cover 13, angling knob 21, and mouthpiece 47. When is stored in the packing case 47, the insertional part cover 11 is wound spirally. The packing material can therefore be designed to be small across. Furthermore, since the operational part cover 12 and others can be stored in the internal space. Storage can be done easily and the internal space can be used efficiently. A very compact packing material ensues.

Next, a procedure of sheathing the endoscope 7 with the endoscope cover 10 will be described.

The insertional part cover 11 is hung on the holding instrument 15, and the dilation tube 14 is coupled with the dilation tube cap 45. Air drawn by the dilator 5 is supplied to the insertional part cover 11. While the endoscope insertion channel 46 is being inflated with air pressure, the coverable endoscope 7 is inserted through the opening 46a of the endoscope insertion channel 46.

The operational part cover 12 is attached, when the universal cord 18, air/water supply channel 38, and suction channel 39 are routed from the endoscope opening 12d to the universal cord opening 12c. The elastic ring 48 is widened radially, the coverable endoscope 7 is inserted into the operational cover 12, and then the widened elastic ring 48 is closed on the circumference of the operational endoscope part locking cap 37.

Next, the universal cord cover 13 is attached. The universal cord 18, air/water supply channel 38, and suction channel 39 are routed through the opening of the universal cord cover 13. The universal cord cover 13 is fitted into the universal cord opening 12c of the operational part cover 12.

Needless to say, a ditch may be formed along the circumference of the operational endoscope part locking cap 37 so that the elastic ring 48 can be locked therein. The cover can then be secured more reliably.

According to the first embodiment, the operational part-side margin of the operational endoscope part locking cap 37 of the insertional part cover 11 and the operational part-side margin 13a of the universal cord cover 13 are shielded with the operational cover 12. The coverable endoscope 7 will therefore not be bared at the border between each pair of cover members. Fingers will therefore not come into contact with the coverable endoscope 7. Bacteria or the like on the coverable endoscope 7 will not adhere to the fingers. Eventually, there will not a fear that the bacteria may adhere to the cover 10 via the fingers. The surface of the coverable endoscope can be kept clean. This results in a user-friendly endoscope cover-sheathed endoscope system. Owing to the elastic ring 48, the operational cover 12 will never turn over.

Figure 6:
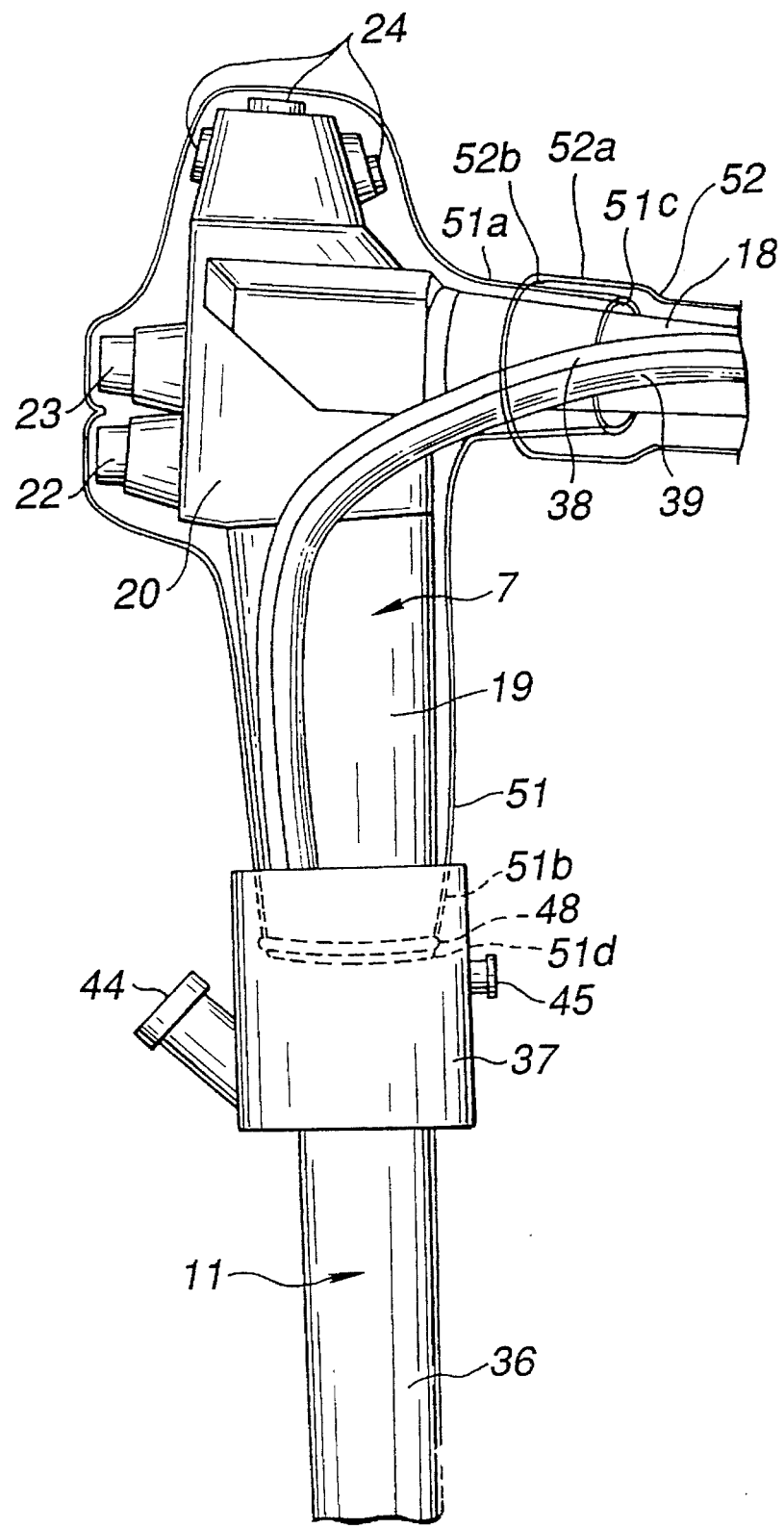
FIG. 6 relates to the second embodiment of the present invention and is an enlarged side view showing a junction between an insertional part cover and an operational part cover and a junction between a universal cord cover and an operational part cover.

FIG. 6 relates to the second embodiment, which is an enlarged side view showing a junction between an insertional part cover and an operational part cover and a junction between a universal cord cover and an operational part cover. The second embodiment is substantially identical to the aforesaid first embodiment. A difference alone will be described.

An insertional part-side margin 51b of an operational part cover 51 is shaped so as to shield part of the portion of the coverable endoscope 7 to be inserted into the operational endoscope part locking cap 37. The operational part-side margin 51b has an endoscope opening 51d for inserting the coverable endoscope 7. The elastic ring 48 that is stretchable radially is provided for the circumference of the endoscope opening 51d.

An operational part cover-side margin 52a of a universal cord cover 52 and an opening 52b of the operational part cover-side margin 52a have a larger diameter than a universal cord-side margin 51a of the operational cover 51. The universal cord-side margin 51a of the operational cover 51 is thus shielded perfectly.

Next, a procedure of sheathing the endoscope 7 with an endoscope cover will be described.

First, the operational part cover 51 is attached to the coverable endoscope 7. Specifically, the universal cord 18 is routed from the endoscope opening 51d to the universal cord opening 51c. The elastic ring 48 is widened radially. The coverable endoscope 7 is inserted through the elastic ring 48. The elastic ring 48 is closed on the portion of the coverable endoscope 7 inserted into the operational endoscope part locking cap 37.

Next, the insertional part cover 11 is attached. When the coverable endoscope 7 is inserted through the opening 46a (See FIG. 3) of the endoscope insertional channel 46, the insertional part-side margin 51b of the operational part cover 51 is inserted together. Thus, the insertional part cover 11 is attached.

Next, the universal cord cover 52 is attached. The universal cord 18, air/water supply channel 38, and suction channel 39 are routed through the universal cord cover 52. The operational part cover-side margin 52a shields the universal cord-side margin 51a of the operational part cover 51. Thus, the universal cord cover 52 is attached.

According to the above second embodiment, two margins of the operational part cover 51 are shielded by the operational endoscope part locking cap 37 and universal cord cover 52 respectively. The second embodiment therefore provides substantially the same advantages as the first embodiment. Since a gap between the operational part cover 51 and coverable endoscope 7 diminishes, the grip 19 of the coverable endoscope 7 can be gripped easily over the operational part cover 51.

Figure 7:
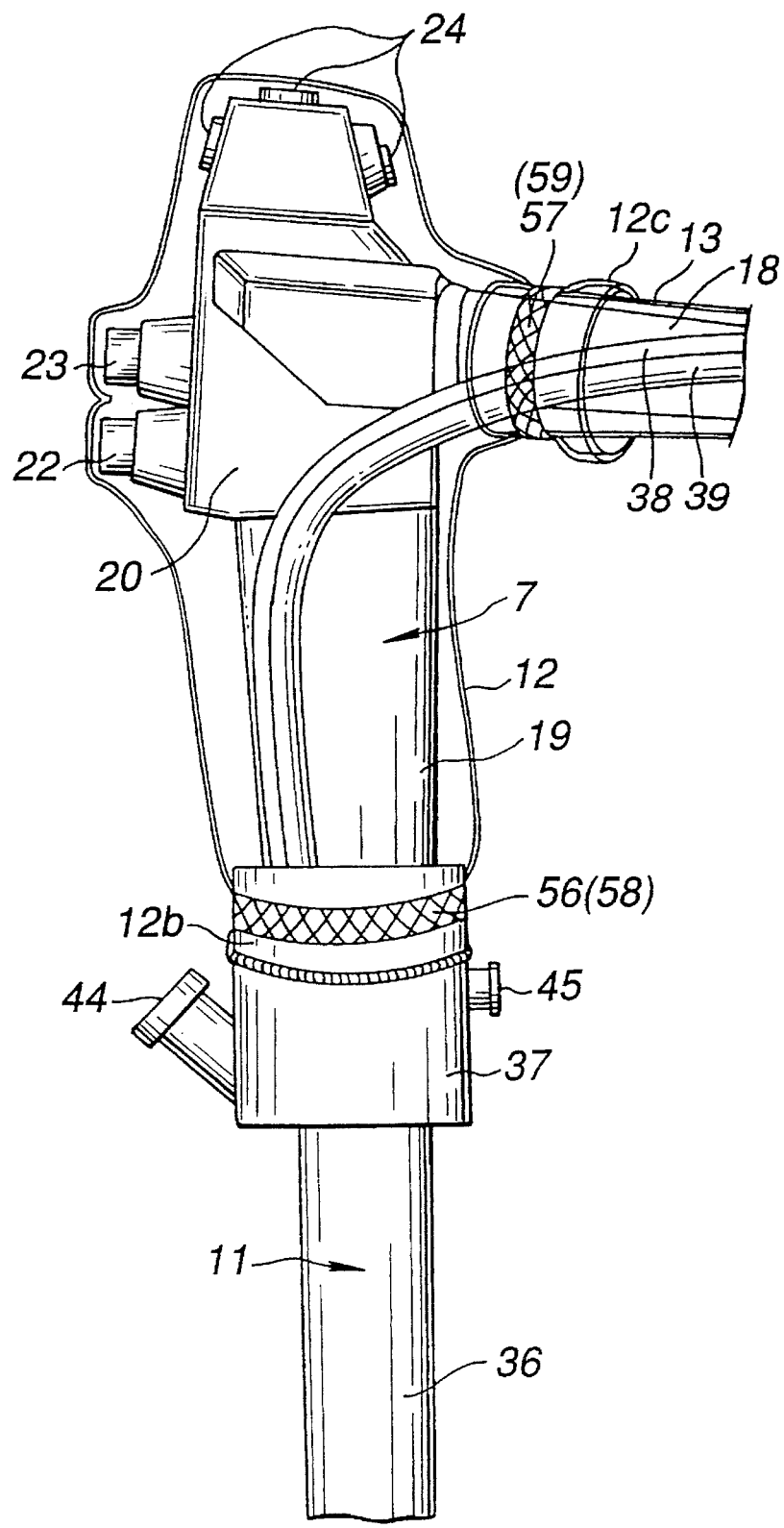
FIG. 7 relates to the third and fourth embodiments of the present invention, and is an enlarged side view showing a junction between an insertional part cover and an operational part cover and a junction between a universal cord cover and an operational part cover.

FIG. 7 relates to the third embodiment of the present invention, which is an enlarged side view showing a junction between an insertional part cover and an operational part cover and a junction between a universal cord cover and an operational part cover. The third embodiment is substantially identical to the aforesaid first or second embodiment. A difference alone will be described mainly.

The operational part-site margin of the operational endoscope part locking cap 37; that is, the portion of the operational endoscope part locking cap 37 covered by the insertional part-side margin of the operational part cover 12 is formed as an adhesive area 56. The portion of the universal cord cover 13 that is inserted into the universal cord opening 12c is also formed as an adhesive area 57. Before use, protective tapes, which are not shown, are adhering to these adhesive areas 56 and 57.

In the third embodiment, a procedure of sheathing the endoscope 7 with the endoscope cover 10 is substantially the same as that in the first embodiment. When the coverable endoscope 7 is sheathed with the cover 10, first, the protective tapes are peeled off. Using the adhesive areas 56 and 57 from which the protective tapes are peeled off, the operational part cover 12 is attached to the operational endoscope part locking cap 37 and universal cord cover 13.

The above third embodiment has substantially the same advantages as the first or second embodiment. Since the margins of adjoining covers are mutually attached with adhesive, the covers will not be deviated from each other.

The fourth embodiment of the present invention will be described with reference to FIG. 7. The fourth embodiment is substantially the same as the aforesaid third embodiment. Only a difference is the structure of the tape in the adhesive area.

To be more specific, the adhesive areas 56 and 57 in the third embodiment are replaced with detachable tapes 58 and 59 in the fourth embodiment.

The above fourth embodiment has substantially the same operation and advantages as the aforesaid third embodiment. When covers are removed, the operational part cover will not be torn out but removed easily.

Figure 8:
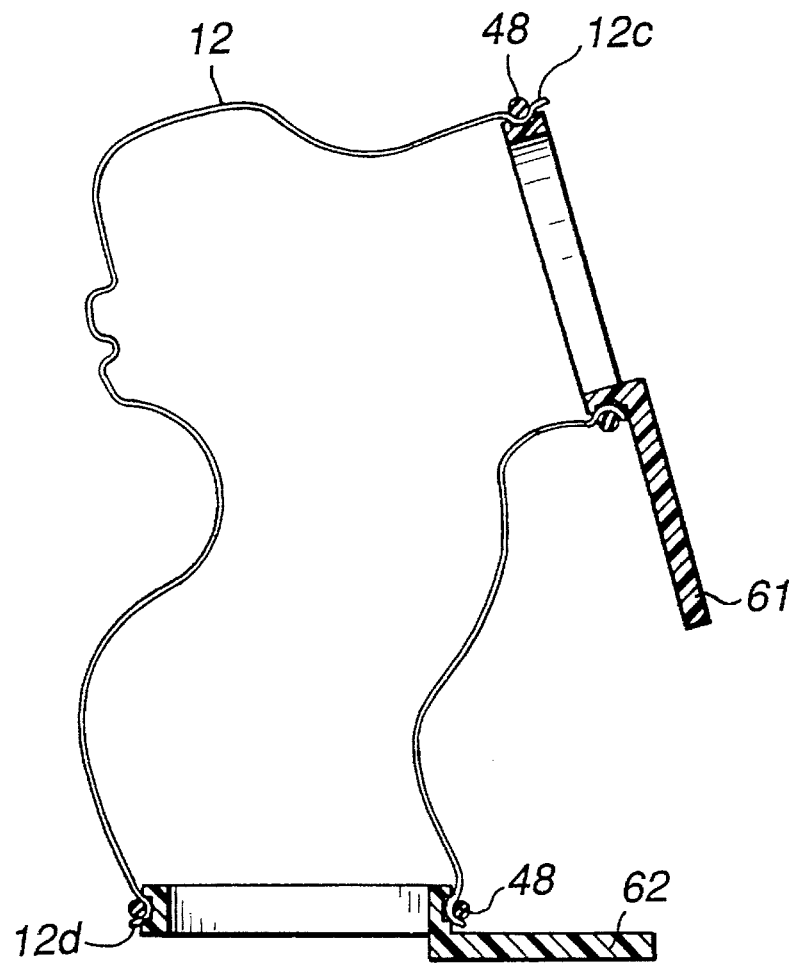
FIGS. 8 to 12 relate to the fifth embodiment of the present invention.
Figure 9:
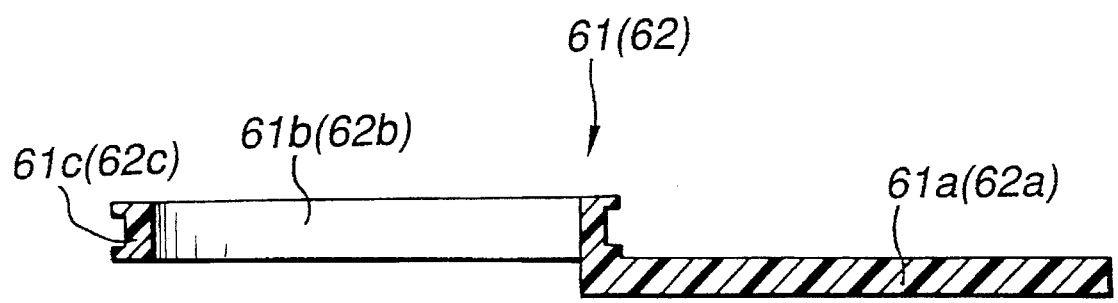
Figure 10:
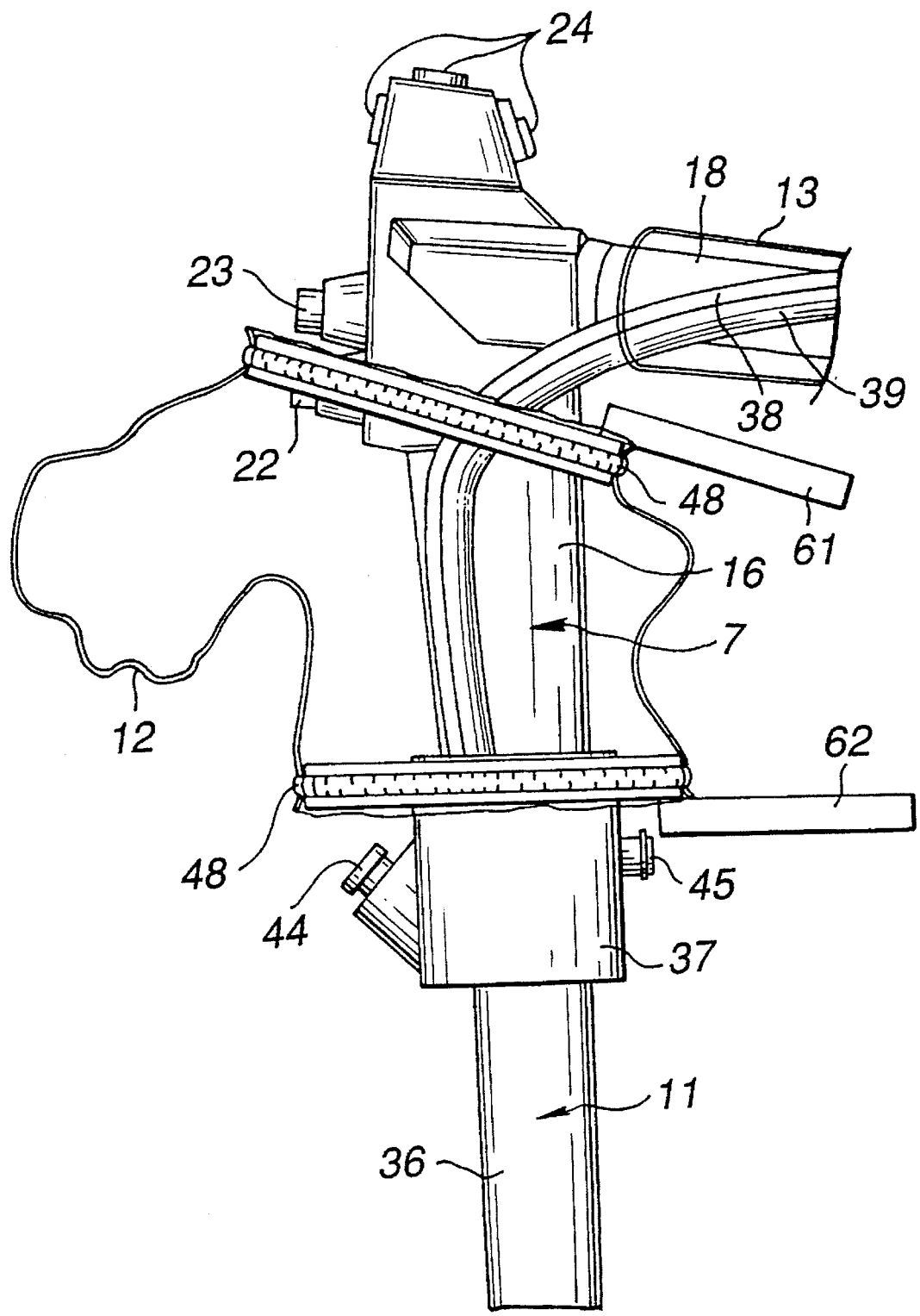
Figure 11:
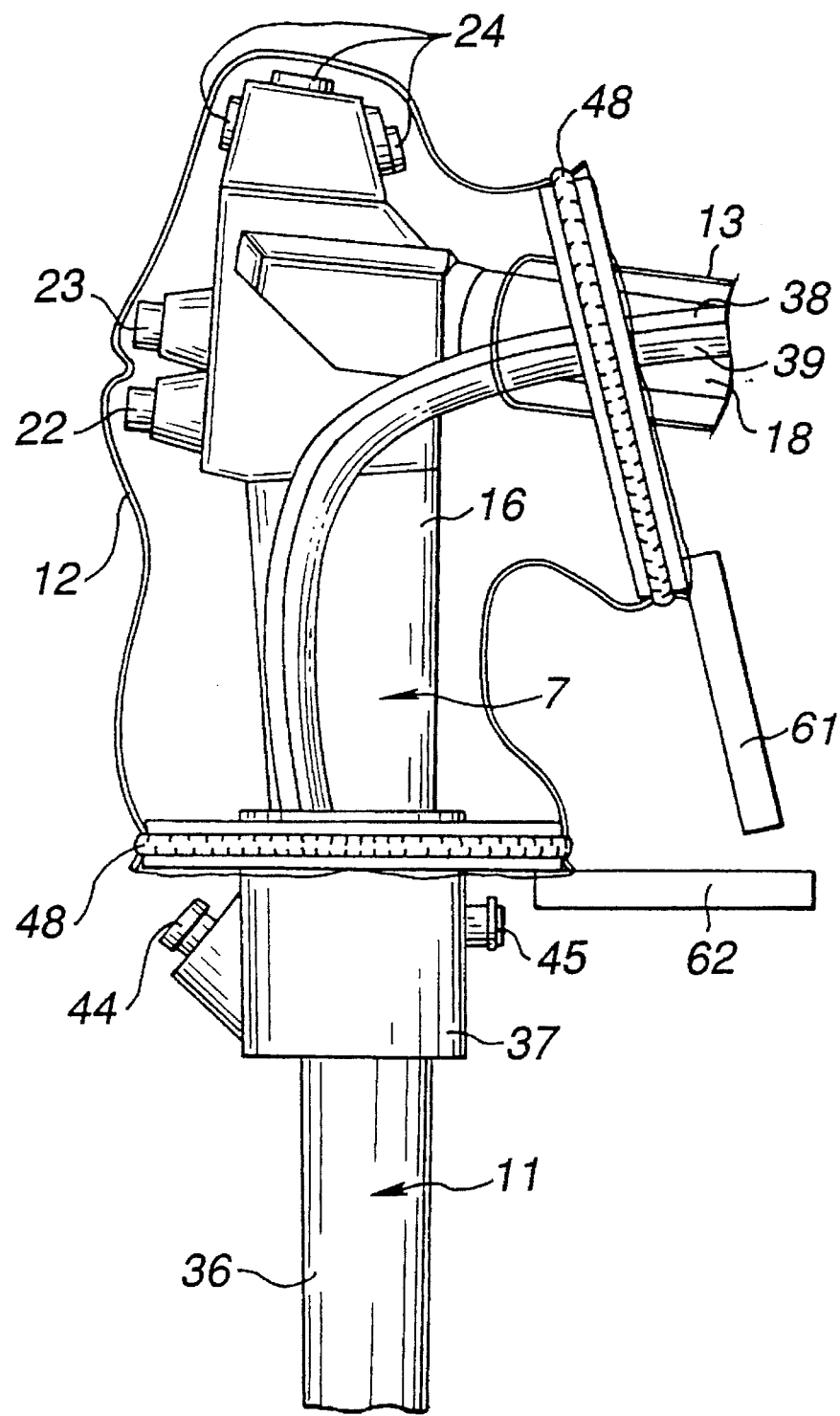
Figure 12:
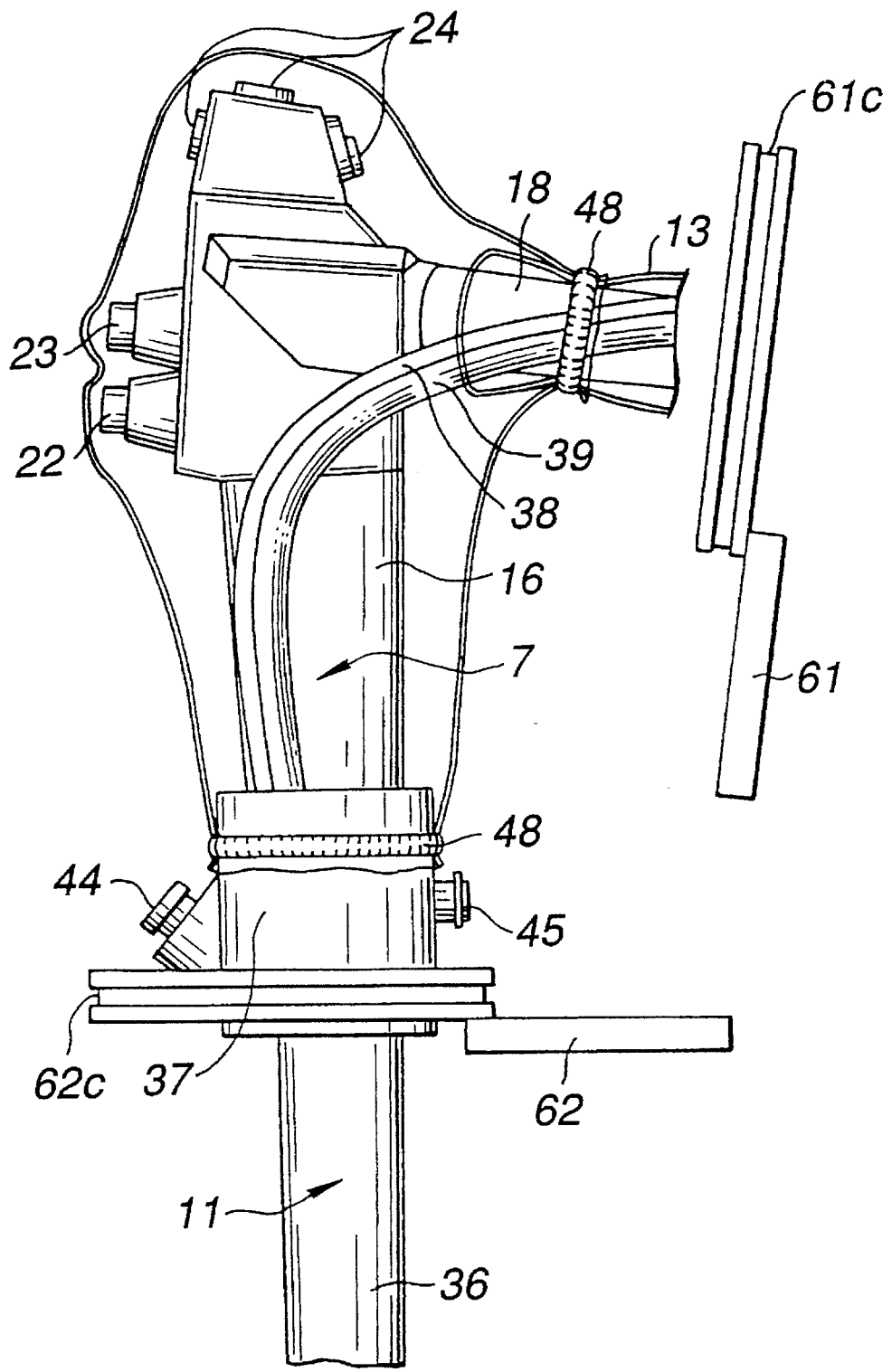

FIGS. 8 to 12 relate to the fifth embodiment of the present invention. FIG. 8 is a longitudinal cross-sectional view showing an operational part cover and attachment jigs for use in attaching the operational part cover to an operational part. FIG. 9 is a longitudinal cross-sectional view showing the attachment jig. FIG. 10 is a side view showing a state in which the attachment jigs are used to start attaching the operational part cover to the operational part. FIG. 11 is a side view showing a state in which the operational part cover is being attached to the operational part using the attachment jigs. FIG. 12 is a side view showing a state in which the operational part cover has been attached to the operational part using the attachment jigs. In the fifth embodiment, the components identical to those in the first to fourth embodiments will not be described.

In the fifth embodiment, a first attachment jig 61 and a second attachment jig 62 are coupled with the universal cord opening 12c and the endoscope opening 12d of the operational part cover 12 using radially-stretchable elastic rings 48.

The first attachment jig 61 (second attachment jig 62) is, as shown in FIG. 9, made of a rigid resin, having an elongated handle 61a (62a) serving as a grip and a short cylindrical attachment 61b (62b). The inner diameter of the attachment 61b (62b) is large enough for the operational part of the coverable endoscope 7 to go through. The outer circumferential surface of the attachment 61b (62b) has a shallow annular ditch 61c (62c) in which the elastic ring 48 is locked.

A procedure of attaching the operational part cover 12 to the operational part 16 using the foregoing attachment jigs 61 and 62 will be described.

First, as shown in FIG. 10, the first attachment jig 61 and second attachment jig 62 are put on the coverable endoscope 7 sheathed with the insertional part cover 11 and universal cord cover 13 through the insertional part 17 (See FIG. 5).

Thereafter, as shown in FIG. 11, the first attachment jig 61 is moved through the operational part 16 of the coverable endoscope 7 to a position at which the margin of the universal cord cover 1.3 is shielded. At this time, the second attachment jig is immobilized at a position at which the margin of the operational endoscope locking cap 37 is shielded.

Finally, the first attachment jig 61 is pulled toward the connector 18a of the universal cord 18, and the second attachment jig 62 is pulled toward the insertional part. The elastic rings 48 are then unlocked from the ring ditches 61c and 62c respectively. Thus, the operational part cover 12 is attached to the coverable endoscope 7 as shown in FIG. 12.

The fifth embodiment has substantially the same advantages as the aforesaid first to fourth embodiments. Furthermore, the operational part cover 12 can be attached effortlessly.

Figure 13:
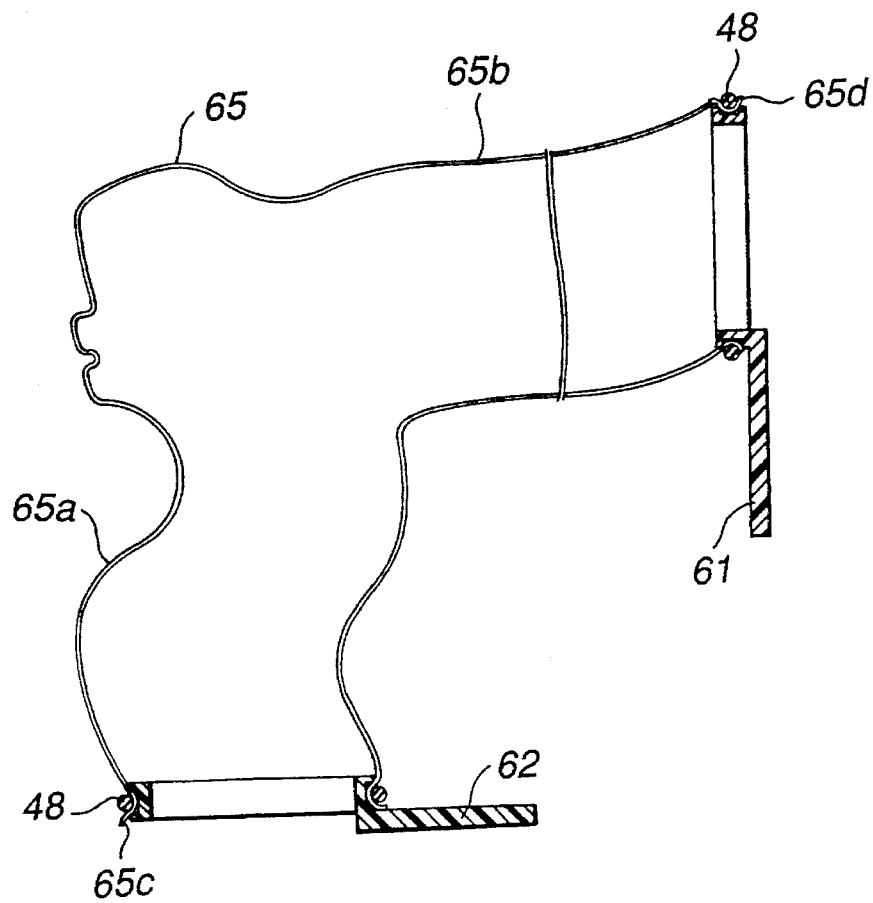
FIG. 13 relates to the sixth embodiment of the present invention and is a longitudinal cross-sectional view showing an operational part universal cord cover and attachment jigs for use in attaching the operational part universal cord cover.

FIG. 13 relates to the sixth embodiment of the present invention, which is a longitudinal cross-sectional view showing an operational part universal cord cover and attachment jigs for use in attaching the operational part universal cord cover. In the sixth embodiment, the components identical to those in the aforesaid first to fifth embodiments will not be described.

In the sixth embodiment, the operational part cover 12 and universal cord cover 13, which are independent of each other in the previous embodiments, are molded in one united body as an operational part universal cord cover 65. The operational part universal cord cover 65 is a sack-like member made of a soft high polymer material, comprising an operational part cover 65a for shielding an operational part and a universal cord cover 65b for shielding a universal cord.

The second attachment jig 62 and the first attachment jig 61 are mounted on the endoscope opening 65c of the operational part cover 65a and the connector opening 65d of the universal cord cover 65b using the elastic rings 48 so as to be dismounted freely.

The foregoing sixth embodiment has the same advantages as the first to fifth embodiments. Since the operational part 16 and the universal cord 18 of the coverable endoscope 7 can be shielded with a single cover of the operational universal cord cover 65, the sheathing workability improves and the number of parts decreases. The prime cost of the cover will eventually plunge down.

Figure 14:
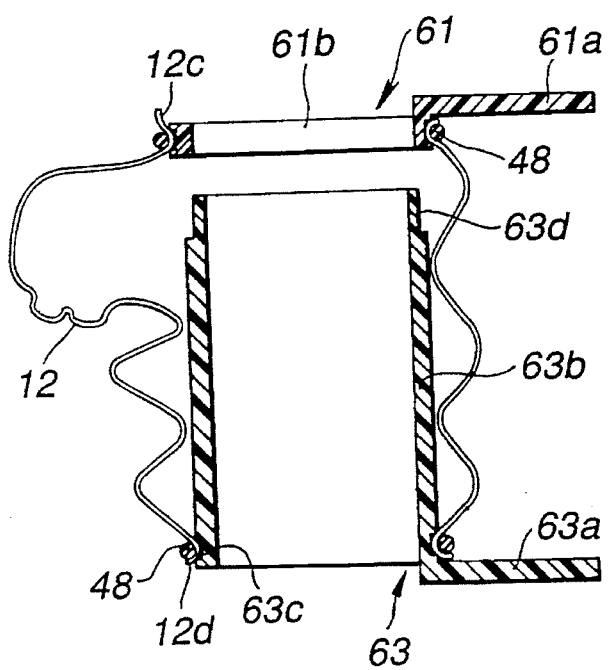
FIG. 14 relates to the seventh embodiment of the present invention and is a longitudinal cross-sectional view showing an operational part cover and attachment jigs for use in attaching the operational part cover to an operational part.

FIG. 14 relates to the seventh embodiment of the present invention, which is a longitudinal cross-sectional view showing an operational part cover and attachment jigs for use in attaching the operational part cover. In the seventh embodiment, the components identical to those in the first to sixth embodiments will not be described.

A second attachment jig 63 in the seventh embodiment has an attachment 63b that corresponds to the attachment 62b of the second attachment jig 62 described in the fifth and sixth embodiments and that is shaped like an axially-long cylinder. A step 63d is formed on the outer circumference of the opening of the attachment 63b on the opposite side of a handle 63a. The second attachment jig 63 can be dismounted from the annular ditch 63c formed along the endoscope opening 12d of the operational part cover 12 by removing the elastic ring 48 locked in the annular ditch 63c.

The inner diameter of the attachment 61b of the first attachment jig 61 that can be dismounted from the universal cord opening 12c is wide enough to fit the step 64.

The procedure of attaching the operational part cover 12 using the attachment jigs in the seventh embodiment is substantially the same as the one in the previous embodiment. After the first attachment jig 61 is mounted on the step 63d of the second attachment jig 63, the attachment jigs are put on the coverable endoscope 7 through the insertional part 17 (See FIG. 5).

The foregoing seventh embodiment can prevent such an incident that the portion of the cover between the first attachment jig and second attachment jig slackens to block the hollow of the cover, and eventually inconveniences a user in sheathing the coverable endoscope 7. In other words, since the first attachment jig 61 is mounted on the second attachment jig 63, the hollow of the cover can be reserved to permit easy sheathing of the coverable endoscope 7. Furthermore, the elongated attachment 63b of the second attachment jig 63 can absorb the slack of the cover.

Needless to say, even when the first attachment jig 61 and second attachment jig 63 in this embodiment are used in conjunction with the operational part universal cord cover 65 in the sixth embodiment, the same advantages as those in this embodiment can be provided.

Figure 15:
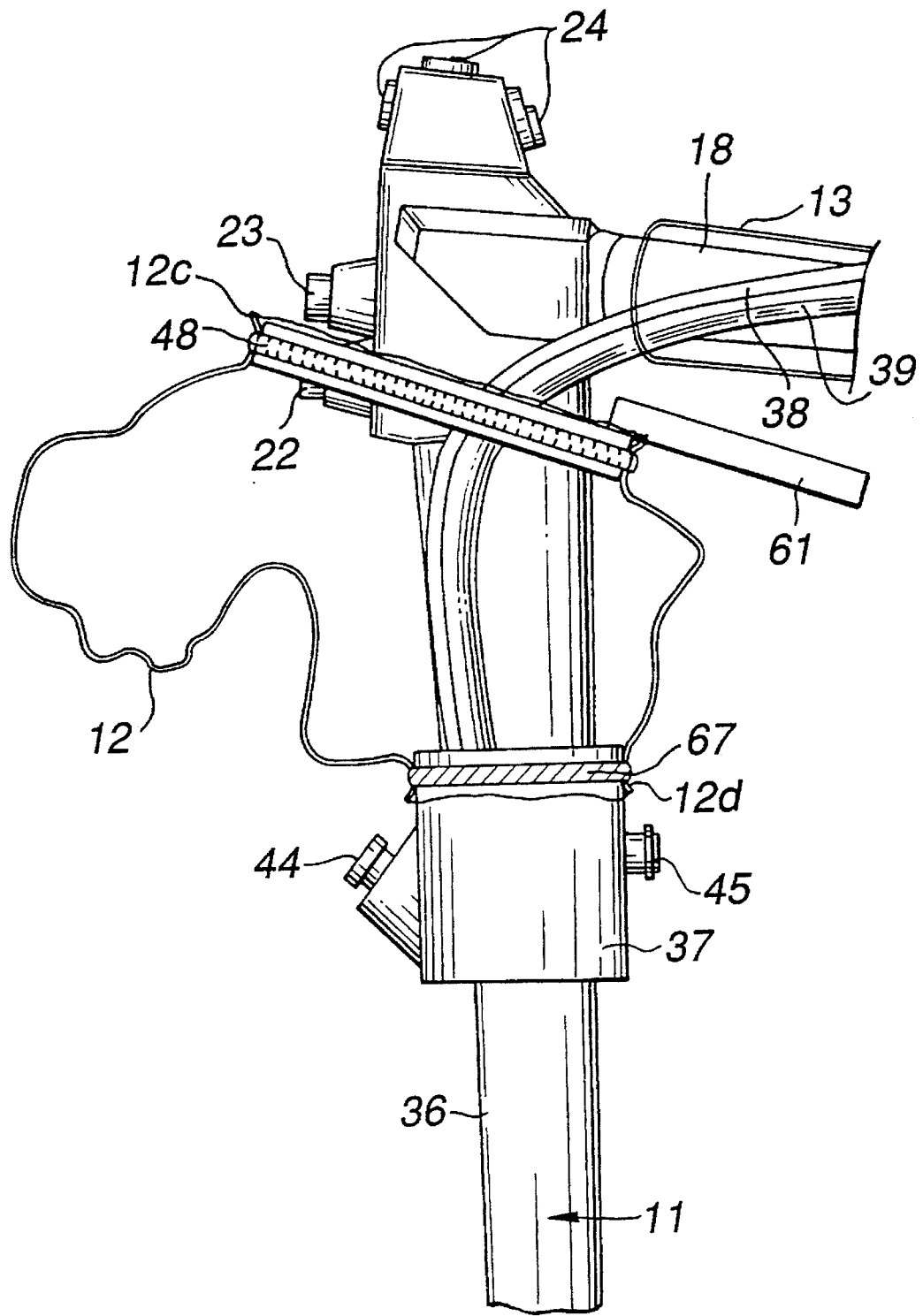
FIG. 15 relates to the eighth embodiment of the present invention and is a side view showing a state in which an attachment jig is used to attach an operational part cover to an operational part.

FIG. 15 relates to the eighth embodiment of the present invention, which is a side view showing a state in which an operational part cover is attached to an operational part using an attachment jig. In this eighth embodiment, the components identical to those in the first to seventh embodiments will not be described.

The endoscope opening 12d of the operational part cover 12 is fixed to the margin of the operational endoscope part locking cap 37 using adhesive 67 or the like. On the other hand, the first attachment jig 61 is mounted on the universal cord opening 12c using the elastic ring 48 so as to be dismounted.

The foregoing eighth embodiment makes it unnecessary to fix the operational part cover 12 to the operational endoscope part locking cap 37. Furthermore, the insertional part cover 11 and operational part cover 12 can be attached at the same time. Since mounting on the first attachment jig 61 need not be done separately, the workability in attaching a cover improves.

Needless to say, even when this embodiment applies to the operational part universal cord cover 65 in the sixth embodiment, the foregoing advantages are available.

Figure 16:
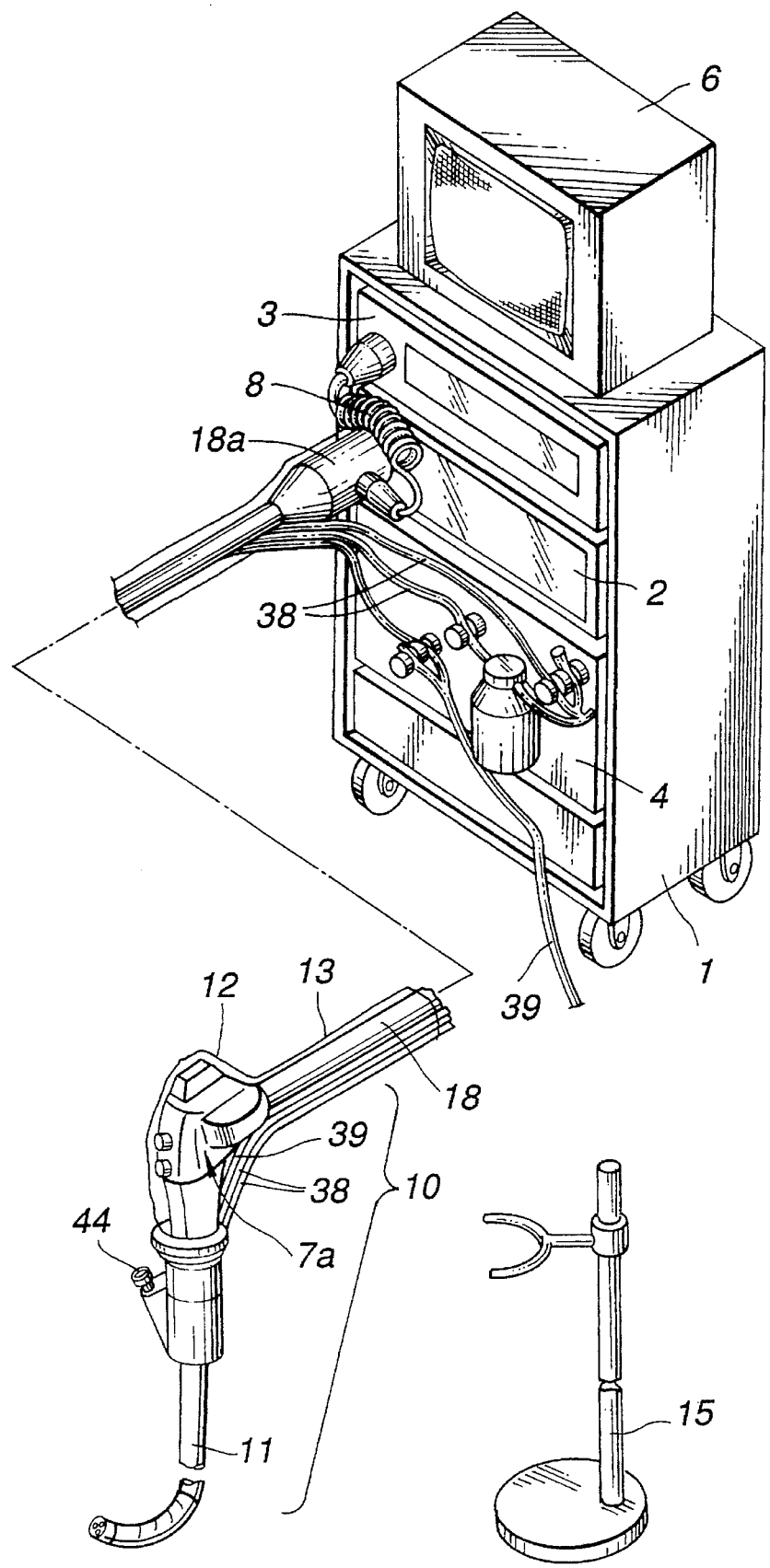
FIGS. 16 to 20 relate to the ninth embodiment of the present invention.
Figure 17:
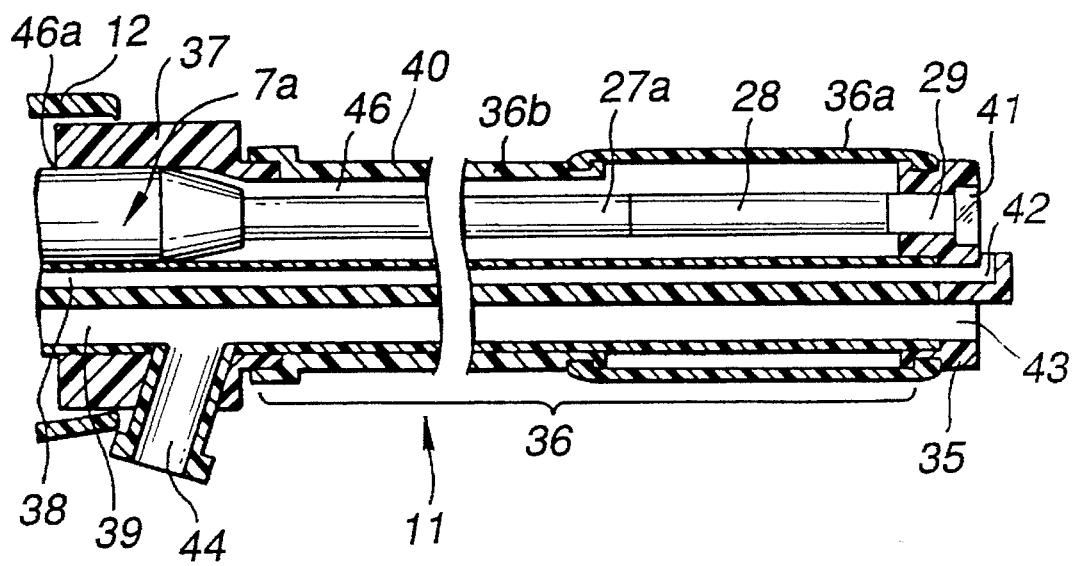
Figure 18:
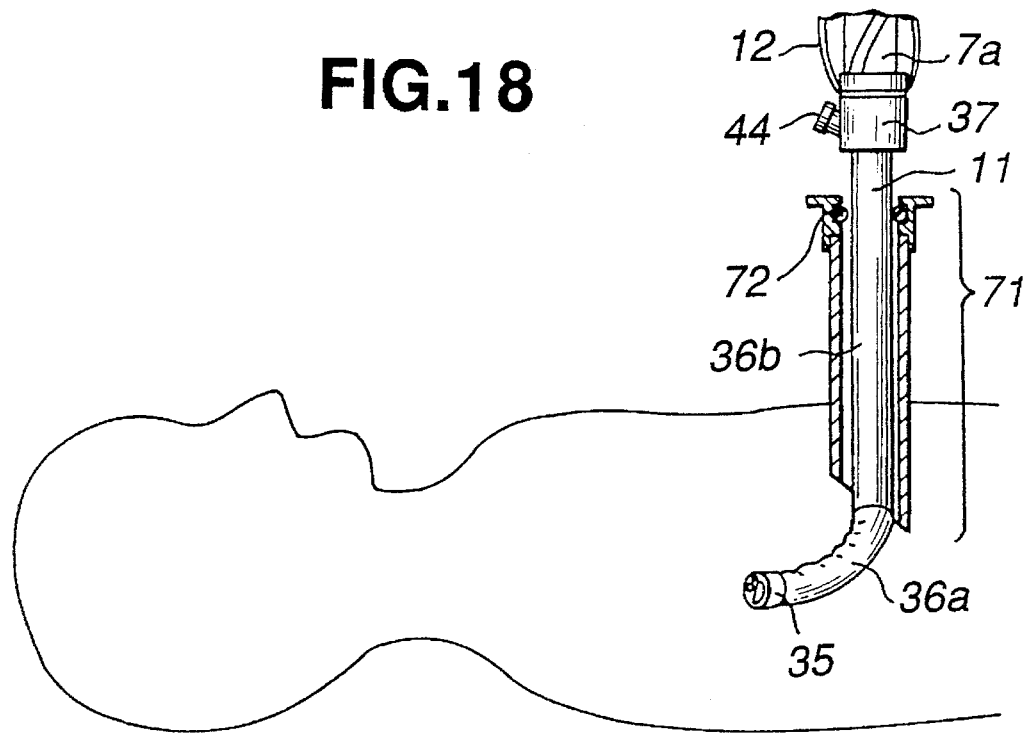
Figure 19:
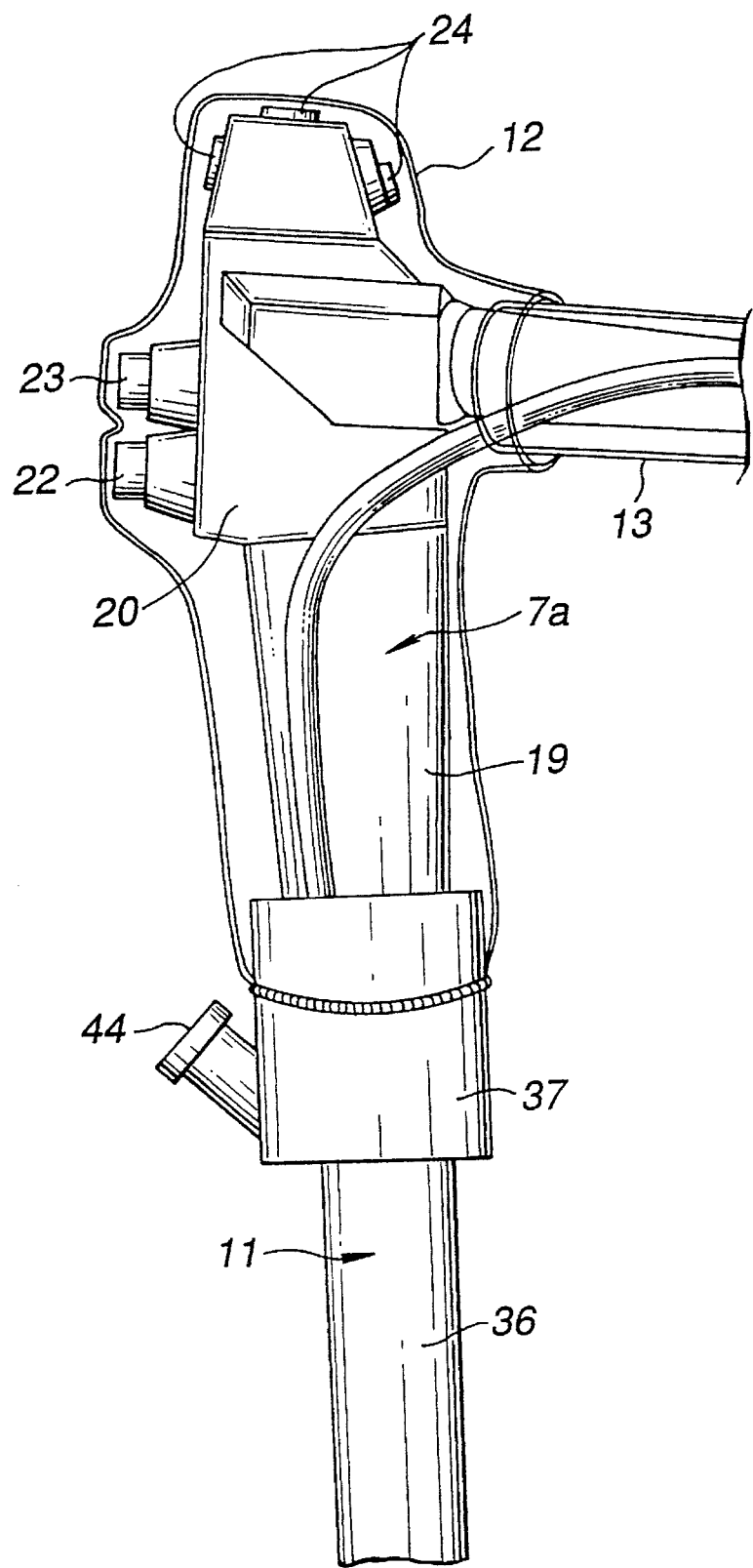
Figure 20:
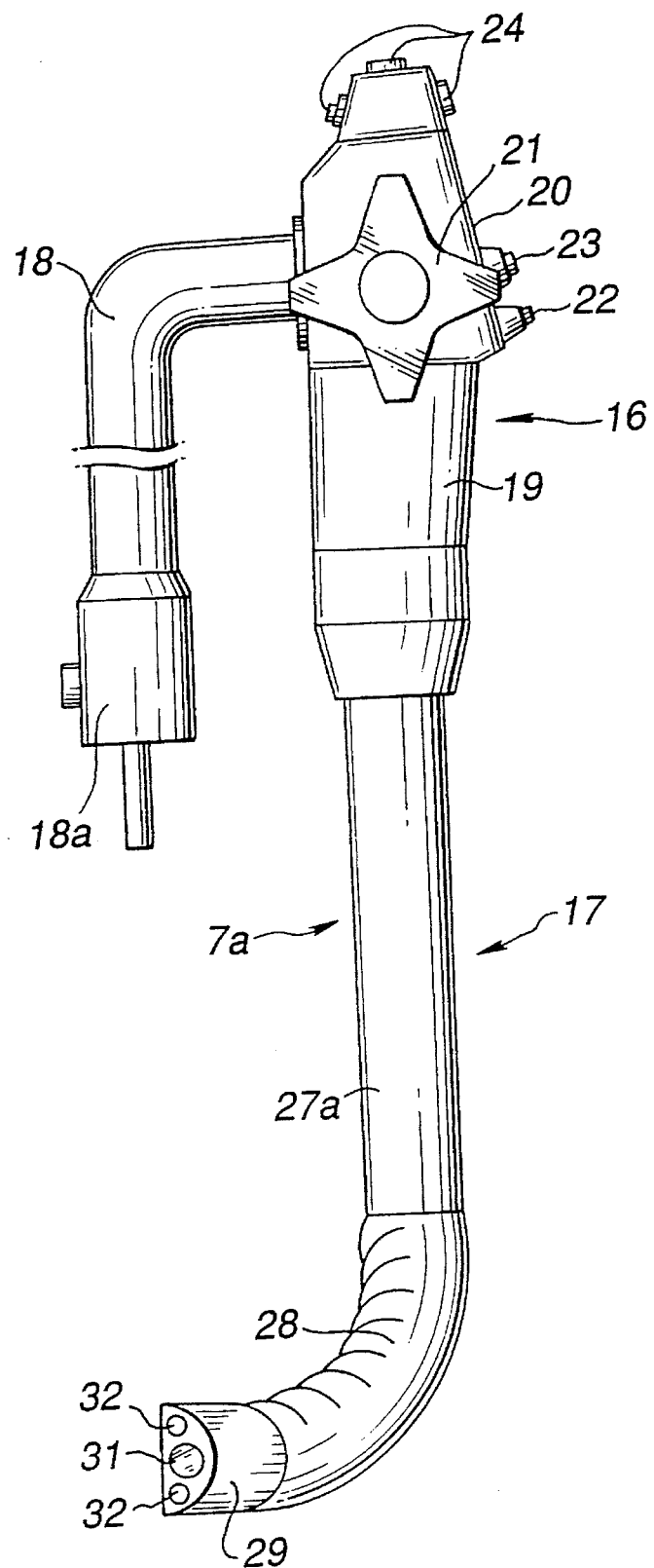

FIGS. 16 to 20 relate to the ninth embodiment of the present invention. FIG. 16 is an oblique view for explaining an overall configuration of an endoscope cover-sheathed endoscope system using an endoscope-cover coverable distally-bending rigid scope. FIG. 17 is a longitudinal cross-sectional view showing an insertional part cover of an endoscope cover (hereinafter, cover) that has been attached to the endoscope-cover coverable distally-bending rigid scope. FIG. 18 is a cross-sectional view showing a scene in which the endoscope-cover coverable distally-bending rigid scope sheathed with the cover is inserted into the abdominal cavity via a rigid sheath. FIG. 19 is an enlarged side view of the endoscope-cover coverable distally-bending rigid scope, showing the junction between the insertional part cover and operational part cover and the junction between the universal cord cover and operational part cover. FIG. 20 is a side view showing the endoscope-cover coverable distally-bending rigid scope.

The endoscope system in the ninth embodiment consists mainly of, for example, a light source apparatus with a built-in light source for illuminating a subject, a video processor 3 for processing signals sent from an imaging device at the distal end of an endoscope, a fluid control apparatus 4 for controlling air/water supply, and a monitor 6 for observing images, which are stored in or placed on a movable cart 1. The light source apparatus 2 is connected to an endoscope-cover coverable distally-bending rigid scope (hereinafter, coverable bending rigid scope) 7a.

The coverable bending rigid endoscope 7a is a rigid scope in which the distal portion of the insertional part can bend. The coverable bending rigid endoscope 7a has, as shown in FIG. 20, an elongated insertional part 17 extending from an operational part 16 formed at the proximal end thereof, and a universal cord 18 extending from the side of the operational part 16. The insertional part 17 comprises a rigid section 27a, a bending section 28, and a distal structure 29, which are concatenated in that order from the proximal end of the insertional part 17. The bending section 28 can be angled by operating an angling knob 21. The distal structure 29 includes an objective optical system 31 and multiple illumination optical systems 32.

A connector 18a is formed at the distal end of the universal cord 18 and plugged in the light source apparatus 2. The connector 18a is, as shown in FIG. 16, also connected to the video processor 3 via a cable 8 extending from the side thereof, thus transmitting and supplying the output signals of an imaging device 96 (See FIG. 26), which is incorporated in the distal structure 29 of the insertional part, to the video processor 8.

In the operational part 16, a grip 19 for gripping a rigid scope 7a is linked with the distal end of an operational part body 20. The operational part body 20 has the angling knob 21, an air/water control switch 22, a suction control switch 23, and an image selection switch 24 for selecting, for example, a still image. The angling knob 21 can be dismounted from the operational part body 20 freely.

An endoscope cover 10 to be attached to the rigid scope 7a consists mainly of, as shown in FIG. 16, an insertional part cover 11 serving as an insertional part shield, an operational part cover 12, and a universal cord cover 3, which are concatenated in that order from the distal end of the endoscope cover. The detail of the insertional part cover 11 of the cover 10 will be described with reference to FIG. 17. The coverable rigid scope 7a is sheathed with the insertional part cover 11 held by a cover holding instrument 15 (See FIG. 16). An endoscope cover-sheathed endoscope (hereinafter, covered endoscope) is the coverable rigid scope 7a sheathed with the cover 10.

As shown in FIG. 17, the insertional part cover 11 consists mainly of a distal part 35, an insertional part cover skin 36, and an operational endoscope part locking cap 37, which are concatenated in that order from the distal end of the insertional part cover. The margins of the insertional part cover skin 36 are coupled with the distal part 35 and operational endoscope part locking cap 37 so as to shut out water and air tightly. An endoscope insertion channel 46 through which the rigid scope 7a runs is formed in the distal part 35, insertional part cover skin 36, and operational endoscope part locking cap 37. An air/water supply channel 38 made of a soft resin, and a suction channel 39 made also of a soft resin are also canalized in the distal part 35, insertional part cover skin 36, and operational endoscope part locking cap 37.

The distal part 35 has an observation window 41, which is made of a transparent resin, facing forward along the optical axes of the objective optical system 31 and illumination optical systems 32 of the coverable rigid scope 7a. Also formed in the distal part 35 includes an air/water nozzle (hereinafter, nozzle) which opens onto a window 41 to wash the rigid scope 7a and communicates with the air/water supply channel 38, and a forceps outlet 43 which communicates with the suction channel 39.

The operational endoscope part locking cap 37 has a forceps insertion port 44 projecting from the side thereof. An opening 46a of the endoscope insertion channel 46 communicates with the proximal end of the cap 37. The air/water supply channel 38 and suction channel 39 are extending beyond the cap 37.

The insertional part cover skin 36 comprises a soft skin 36a for shielding the bending section 28 of the coverable bending rigid scope 7a, and a rigid skin 36b serving as a rigid shield for shielding the rigid section 27a. The soft skin 36a is made of a soft high polymer material and very thin (for example, approximately 0.1 to 3 mm). The rigid skin 36b is made of a relatively rigid resin such as Teflon or urethane. The soft skin 36a and rigid skin 36b are linked with each other so as to shut out water and air tightly. The outer surface of the rigid skin 36b is realized as a low-friction surface 40 which has undergone low-friction processing.

At the junction between the insertional part cover 11 and operational part cover 12, or between the universal cord cover 13 and operational part cover 12, as shown in FIG. 19, the adjoining margins overlap each other. The underlying rigid scope 7a will therefore not be exposed to outside.

FIG. 18 shows a scene in which the coverable bending rigid scope 7a sheathed with the cover 10 is inserted into a rigid sheath 71 to observe the abdominal cavity. The rigid sheath 71 may be referred to as a trocar, which has been proposed in various types and become popular.

When the rigid scope 7a is inserted into the rigid sheath 71 to observe the abdominal cavity, the abdominal cavity must be inflated with air for better visualization and held inflated with a field of view focused. The proximal end of the rigid sheath 71 is provided with an airtight packing 72 for retaining airtightness. When the rigid scope 7a is inserted, the airtight packing 72 prevents air from leaking out of the abdominal cavity. It is, as described previously, the rigid skin 36b that comes into contact with the airtight packing 72. The rigid skin 36b can withstand the frictional force resulting from the rubbing against the airtight packing 72 and will not be damaged. The rigid skin 36b should be rigid enough to withstand the frictional force resulting from the rubbing against the airtight packing 72. The rigid skin 36b need not therefore be made of a material having a perfect rigidity; such as, a metal.

The ninth embodiment is not limited to the coverable bending rigid scope, but can apply to an uncovered bending rigid scope or a flexible scope which is usually used without a cover. The embodiment can also apply to a laparoscopic ultrasound probe, which is sheathed with a cover, for use in ultrasonic evaluation of the organs in the abdominal cavity. For a flexible scope, a soft skin may be used as the cover skin for shielding a bending section or a flexible tube that need to be bent, and a rigid skin may be used as the cover skin for shielding the other portions of an insertional part. As for a non-bending rigid scope, the cover skin for shielding the insertional part may, of course, entirely be realized with a rigid skin.

According to the foregoing ninth embodiment, since the airtight packing 72 of the rigid sheath 71 and the rigid skin 36b of the insertional part cover 11 are in close contact with each other. Even when the coverable bending rigid scope 7a is operated, airtightness can be ensured and air will not leak out of the abdominal cavity. It is the rigid skin 36b that rubs against the airtight packing 72 of the cover skin 36. Wrinkles resulting from friction with the airtight packing 72 will therefore not occur. The cover skin 36 will not be pierced or damaged. The endoscope lying in the endoscope cover will never be exposed to outside. Even if bacteria adhere to the endoscope, the bacteria will not invade into the patient's body cavity. The patient will therefore not contract infection. Furthermore, since the cover has a rigid portion, sheathing or unsheathing become simpler than that when an endoscope is sheathed with or unsheathed from an entirely-soft cover. Moreover, the insertional part cover 11 for shielding the bending section 28 of the coverable bending rigid scope 7a is realized with the soft skin 36a. Angling will therefore not be crippled. The outer surface of the rigid skin 36b of the insertional part cover 11 is formed as the low-friction surface 40, which permits simple insertion into the rigid sheath 71 or the like. Besides, the damage on the cover resulting from friction can be suppressed more effectively.

Figure 21:
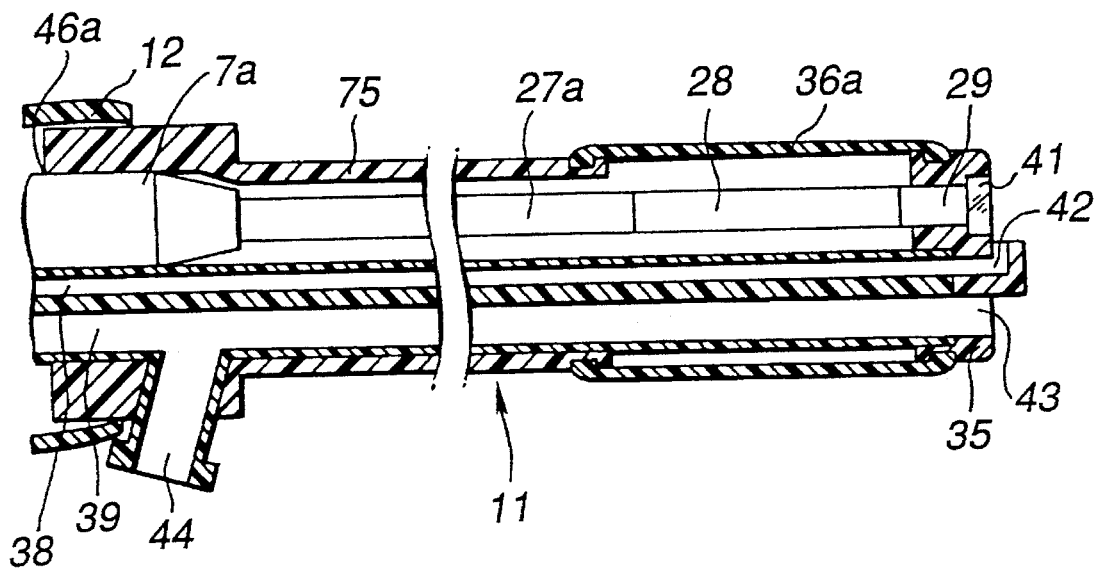
FIG. 21 relates to the tenth embodiment of the present invention and is a longitudinal cross-sectional view showing an insertional part cover of an endoscope cover attached to an endoscope-cover coverable distally-bending rigid scope.

FIG. 21 relates to the tenth embodiment of the present invention, which is a longitudinal cross-sectional view showing an insertional part cover of an endoscope cover which has been attached to an endoscope-cover coverable distally-bending rigid scope. The tenth embodiment is substantially identical to the ninth embodiment. A difference alone will be described.

In the tenth embodiment, the operational endoscope part locking cap 37 and rigid skin 36b in the ninth embodiment are molded in a united body so as to provide an operational endoscope part locking rigid skin 75 serving as a rigid shield. The other components are identical to those in the ninth embodiment.

The foregoing tenth embodiment has substantially the same advantages as the ninth embodiment. Besides, since the number of parts decreases, the assembling workability improves and the prime cost lowers.

Figure 26:
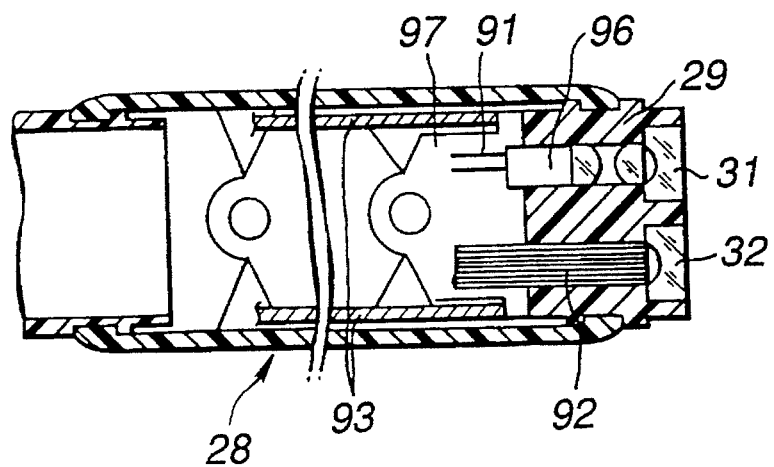
FIGS. 22 to 26 relate to the eleventh embodiment of the present invention.
Figure 22:
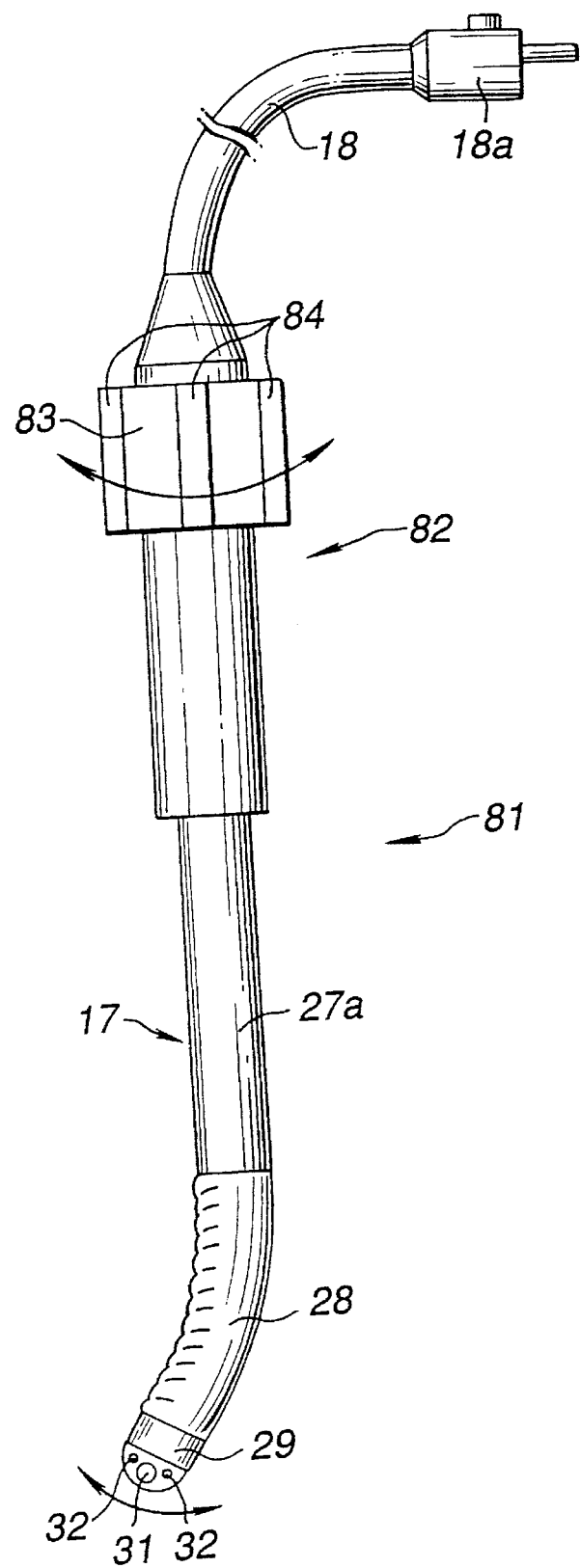
Figure 23:
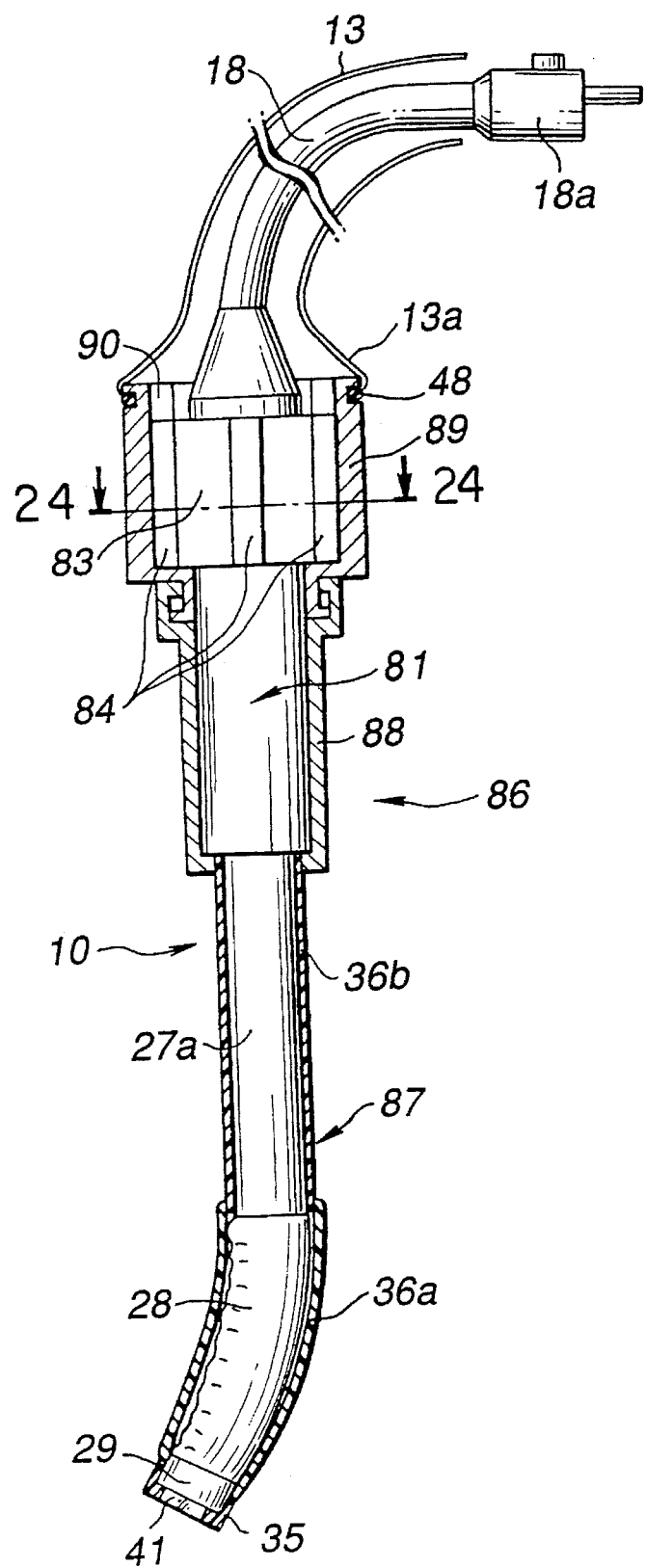
Figure 24:
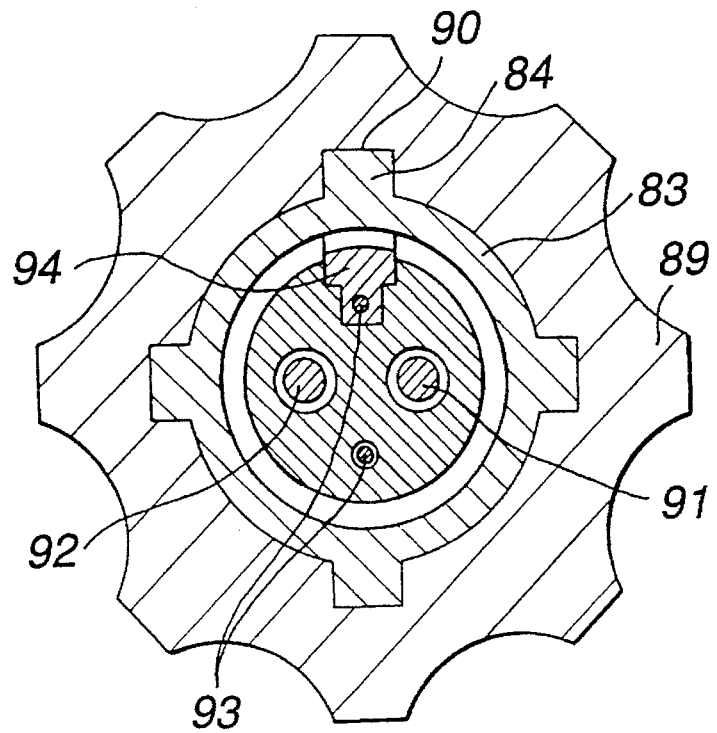
Figure 25:
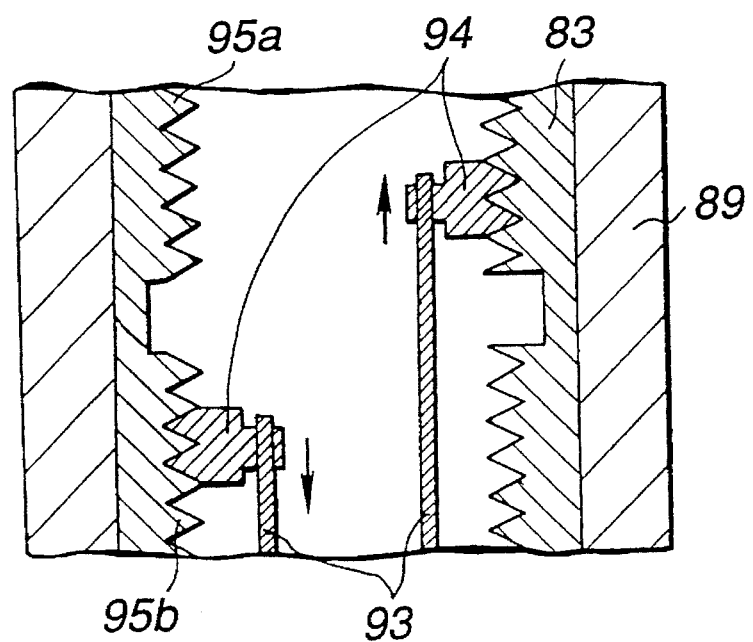

FIGS. 22 to 26 relate to the eleventh embodiment of the present invention. FIG. 22 is a side view showing other example of an endoscope-cover coverable distally-bending rigid scope. FIG. 23 is a longitudinal cross-sectional view showing a state in which the endoscope-cover coverable distally-bending rigid scope has been sheathed with an endoscope cover. FIG. 24 shows an A—A cross section of FIG. 23. FIG. 25 is a longitudinal cross-sectional view showing an angling mechanism schematically. FIG. 26 is a longitudinal cross-sectional view showing the vicinity of the distal part of the endoscope-cover coverable distally-bending rigid scope.

A coverable bending rigid scope 81 in the eleventh embodiment has, as shown in FIG. 22, an insertional part 17 extending from an operational part 82 toward the distal end thereof, and a universal cord 18 extending from the operational part 82 toward the proximal end thereof.

The operational part 82 has an angling section 83. Convex areas 84 are formed on the circumferential surface of the angling section 83. The bending section 28 is angled by turning the angling section 83 radially (the angling mechanism will be described later).

As shown in FIG. 23, the cover 10 with which the coverable bending rigid scope 81 is sheathed comprises a universal cord cover 13 for shielding the universal cord 18, and an operational part/insertional part cover 86 for shielding the operational part 82 and insertional part 17.

The operational part/insertional part cover 86 is composed of an insertional part cover 87, an operational endoscope part locking cap 88, and an angle ring 89, which are concatenated in that order from the distal end to the proximal end of the operational part/insertional part cover.

The insertional part cover 87 consists of a rigid skin 36b, a soft skin 36a, and a distal part 35. The distal part 35 has a transparent observation window 41 facing forward along the optical axes of the optical systems of the coverable bending rigid scope 81. The soft skin 36a shields the bending section 28, and the soft skin 36b shields the rigid section 27a. The distal part 35, soft skin 36a, rigid skin 36b, and operational endoscope part locking cap 88 are linked with one another airtightly.

The angle ring 89 is coupled with the operational endoscope part locking cap 88 so as to be rotatable freely. The inside of the angle ring 89 has concave areas 90 with which the convex areas 84 of the angling section 83 are engaged. When the angle ring 89 is turned radially, the angling section 83 therefore rotates unitedly. Thus, angling is achieved.

FIG. 24 shows a longitudinal cross section of a portion involved with the angling.

As illustrated, an imaging cable 91 for transmitting signals fed by an imaging device 96 shown in FIG. 26, a light guide 92 for propagating illumination light from the light source apparatus 2, and angling wires 93 that are fixed to an angling top 97 at the extremely distal end and that when towed, angle the bending section 28 of the coverable distally-bending rigid scope 81 are running through the angling section 83. The other end of the angling wires 93 are fixed to helicoid tops 94 which will be described later.

Next, referring to FIG. 25, the angling mechanism will be described.

Two helicoid areas 95a and 95b are formed on the inner circumferential surface of the angling section 83. The orientations of these helicoids are opposite to each other. The two helicoid tops 94 are engaged with the helicoid areas 95a and 95b. The helicoid tops 94 are, as described previously, coupled with ones of the ends of the angling wires 93. The helicoid tops 94 are, as shown in FIG. 24, restricted in radial rotation and allowed merely to move axially.

When the angling mechanism having the foregoing structure is used for angling, first, an operator turns the angle ring 89. The angling section 83 then turns unitedly, and the helicoid areas 95a and 95b formed on the inner circumferential surface thereof turns. The helicoid areas 95a and 95b are ditched, as described above, to orient in the opposite directions. The rotation causes one of the helicoid tops 94, which are engaging with the helicoid areas 95a and 95b, to move tip axially and the other one to move down axially. With the movements of the helicoid tops 94, the angling wires 93 are towed to trigger angling.

The universal cord cover 13 shown in FIG. 23 is a sack-like member whose both ends are closed. The operational part-side margin 13a of the universal cord cover 13 opens widely to accept the angle ring 89. The operational part-side margin 13a is fixed to the end of the angle ring 89 using the elastic ring 48.

The foregoing eleventh embodiment has substantially the same advantages as the aforesaid ninth and tenth embodiments. With only one member of the operational part/insertional part cover 86, the insertional part 17 and operational part 82 of the coverable bending rigid scope 81 can be shielded. Moreover, the angling section 83 can also be sheathed together, thus permitting excellent workability in attaching a cover. Furthermore, angling can be done easily.

In the previous embodiments, the processing for smoothening the surface of the insertional shield, which is described in the tenth embodiment, will reduce the occurrence of friction with other member. Needless to say, lubricant may be applied to the surface.

In the present invention, it will be apparent that a wide range of different modes can be formed on the basis of the invention without departing from the spirit and scope of the invention. This invention is not restricted to any specific embodiment but is limited to the appended claims.

What is claimed is:

1. An endoscope cover-sheathed endoscope system, comprising:

an endoscope;

an endoscope cover including an operational part cover covering an operational part of an endoscope, an insertional part cover covering an insertional part of an endoscope, and a universal cord cover covering both a fluid channel having one end opening near a distal end of said insertional part cover and another end supplying and discharging fluid and a universal cord of an endoscope for shielding said endoscope wherein said operational part cover overlaps and shields the margin of said insertional part cover to prevent exposing said underlying endoscope to the outside at a junction between said operational part cover and said insertional part cover constituting said endoscope cover and wherein the operational part-side margin of said insertional part cover is shielded by part of said operational part cover.

2. An endoscope cover-sheathed endoscope system according to claim 1, wherein at least one of said operational part cover and said insertional part cover is provided with a securing means for securing the other cover member.

3. An endoscope cover-sheathed endoscope system according to claim 2, wherein said securing member is an elastic ring for fastening said operational part cover on said insertional part cover member.

4. An endoscope cover-sheathed endoscope system according to claim 2, wherein said securing member is an adhesive area formed in an area in which said operational part cover and said insertional part cover overlap each other.

5. An endoscope cover-sheathed endoscope system according to claim 2, wherein said securing member is a detachable tape attached to an area in which said operational part cover and said insertional part cover overlap each other.

6. An endoscope cover-sheathed endoscope system according to claim 1, wherein said endoscope is an endoscope dedicated to an endoscope cover.

\* \* \* \* \*